(12) United States Patent
Che et al.

(10) Patent No.: US 10,281,402 B2
(45) Date of Patent: May 7, 2019

(54) DEVICES AND METHODS FOR IMAGING BIOMOLECULES

(71) Applicant: Azure Biosystems, Inc., Dublin, CA (US)

(72) Inventors: Diping Che, San Ramon, CA (US); Zhefu Zhang, Beijing (CN)

(73) Assignee: Azure Biosystems, Inc., Dublin, CA (US)

( * ) Notice: Subject to any disclaimer, the term of this patent is extended or adjusted under 35 U.S.C. 154(b) by 0 days.

(21) Appl. No.: 15/880,531

(22) Filed: Jan. 26, 2018

(65) Prior Publication Data

US 2018/0209908 A1  Jul. 26, 2018

Related U.S. Application Data

(63) Continuation of application No. 62/450,699, filed on Jan. 26, 2017.

(51) Int. Cl.
| | | |
|---|---|---|
| *G01N 21/64* | (2006.01) | |
| *C12Q 1/6816* | (2018.01) | |
| *G01N 33/58* | (2006.01) | |
| *G01N 33/60* | (2006.01) | |
| *G06T 7/00* | (2017.01) | |
| *G01J 3/44* | (2006.01) | |
| *H04N 5/372* | (2011.01) | |
| *G06T 7/90* | (2017.01) | |

(52) U.S. Cl.
CPC ........ *G01N 21/6458* (2013.01); *C12Q 1/6816* (2013.01); *G01J 3/4406* (2013.01); *G01N 21/6428* (2013.01); *G01N 33/582* (2013.01); *G01N 33/60* (2013.01); *G06T 7/0012* (2013.01); *G01N 21/6452* (2013.01); *G01N 21/6456* (2013.01); *G01N 2021/6419* (2013.01); *G01N 2021/6441* (2013.01); *G01N 2201/06113* (2013.01); *G06T 7/90* (2017.01); *G06T 2207/10024* (2013.01); *G06T 2207/10064* (2013.01); *H04N 5/372* (2013.01)

(58) Field of Classification Search
CPC .......... G01N 21/6458; G01N 21/6428; C12Q 1/6816
See application file for complete search history.

(56) References Cited

U.S. PATENT DOCUMENTS

| 2009/0226950 A1* | 9/2009 | Cunningham ..... G01N 21/6452 435/29 |
| 2015/0069267 A1* | 3/2015 | Feng ................. G01N 21/6428 250/459.1 |

* cited by examiner

*Primary Examiner* — Hugh Maupin
(74) *Attorney, Agent, or Firm* — Incubate IP; Randy R. Micheletti

(57) ABSTRACT

The present disclosure provides devices and methods enabling the analysis of biomolecules. In some embodiments, the biomolecules may be DNA, RNA, protein, peptide, small molecule, catalyst, precursor, nucleotide, antibodies, or other biomolecules of interest.

15 Claims, 14 Drawing Sheets

| Emitter/Dye | Light Source | Detector | Emission Filter | Beam Splitter |
|---|---|---|---|---|
| Green excitable dyes | 118: 525nm Diode | 122: Photomultiplier tube | 108: Single bandpass 570/30 | 114: Pass 540+ |
| NIR excitable dyes | 120: 780nm Diode | 124: avalanche photodiode | 110: Single bandpass 830/50 | 116: pass 790+ |
| | | | | 112: pass 680+ |

| Emitter/Dye | Light Source | Detector | Emission Filter | Beam Splitter |
|---|---|---|---|---|
| Red excitable dyes | 120: 635nm Diode | 124: avalanche photodiode | 110: Single bandpass 705/60 | 116: pass 640+ |
| Blue excitable dyes | 118: 473nm Diode-pumped solid state (DPSS) laser | 122: photomultiplier tube | 108: Dual bandpass 390/40 & 510/30 | 114: Dual band pass 430-, 480+ |
| Phosphor | 120: 635nm Diode | 122: photomultiplier tube | 108: Dual bandpass 390/40 & 510/30 | 114: Dual bandpass 430-, 480+ |
| | | | | 112: pass 570+ |

FIG. 4

DEVICES AND METHODS FOR IMAGING BIOMOLECULES

PRIORITY CLAIM

This application claims priority to U.S. Provisional Patent Application Ser. No. 62/450,699, filed Jan. 26, 2017, the entire contents of which is incorporated herein by reference and relied upon.

BACKGROUND

Spatially resolving biomolecules in two dimensions on a substrate is an important tool in molecular biology. Components of complex mixtures of biomolecules can be spatially resolved on a gel or blot and imaged or scanned to measure levels of specific biomolecules of interest. Likewise, biomolecules may be bound to an array, or spatially segregated in wells of a microtiter plate and may again be measured by imaging or scanning. Different methods of labeling biomolecules require different measurement techniques to read out the analysis.

One method of imaging fluorescent molecules is to use an optical scan head, where an objective lens is linked to a light source and detectors through a series of beam splitters and filters designed to enable detection of a certain fluorophore or phosphor. This directs light of a particular wavelength range to excite a fluorophore or phosphor, and directs the emitted light selectively through to a detector. This scan head may be moved along the 2-dimensional axes of the substrate in order to get a high-resolution readout of fluorescence for the entire substrate. Or in some cases, the substrate may be moved in 2-dimensions in front of the objective.

It is not unusual to combine fluorescent and phosphorescent detection into a single device. Having a dedicated instrument for each technique can be expensive to acquire and maintain, and will take up precious space in a laboratory. Having multiple readouts creates a flexible instrument, also allows interrogation of multiple biomolecules simultaneously. However, enabling the detection of multiple "colors" of fluorescence and phosphor can increase the number of scanning heads, adding complexity and cost to the instrument, and can lead to reduced sensitivity if there is overlap between the excitation and emission wavelengths of 2 fluorophores measured with the same optical scan head.

Scanning often involves placing a substrate on a scanning bed that is considerably larger than the substrate. Scanning the entire scan bed results in wasted time and data storage for the scanning of the region surrounding the substrate.

A need therefore continues to exist for improved biological substrate analyzers and methods of analyzing biological substrates. The present disclosure meets this need.

SUMMARY

The present disclosure provides devices and methods enabling the analysis of biomolecules. In particular, the instruments disclosed herein enable convenient and efficient scanning and imaging of a biological substrate using multiple wavelengths of light (e.g., two or more of fluorescent, chemiluminescent, colorimetric, and phosphor light). In some embodiments, the biomolecules may be DNA, RNA, protein, peptide, small molecule, catalyst, precursor, nucleotide, antibodies, or other biomolecules of interest.

In some embodiments, the biomolecules will be contained on or in a substrate. In some embodiments, these biomolecules will be separated and encased in a gel. This gel can be made of any polymer such as agarose, polyacrylamide, starch, or any other polymer which can act as a sieving matrix or as a support, for the separation of biomolecules. In some embodiments, the biomolecules will be transferred from a gel to a membrane made of nitrocellulose, polyvinylidene fluoride (PVDF), or other material capable of non-specifically binding the biomolecules of interest, before the imaging step. In some embodiments, the biomolecules will be in a 2-dimensional array, bound to the surface, or within a microtiter plate.

In some embodiments biomolecules of interest will be labeled with fluorescent moieties. In some embodiments, an enzyme will be linked to the biomolecules which can generate a chemiluminescent, fluorescent, or chromogenic/colorimetric label. In some embodiments, biomolecules will be directly labeled with radioactive atoms. In some embodiments, a substrate containing radiolabeled biomolecules placed on a photostimulable luminescence plate, or, phosphorimaging screen, which can then be scanned. In some embodiments, labeled antibodies will be used to selectively label biomolecules of interest.

In some embodiments, more than one scanning or imaging technique will be enabled in a single device. In some embodiments, a single device will enable scanning fluorescent dyes, phosphor imaging, optical densitometry, chemiluminescence, and colorimetric analysis. In some embodiments, a single device will enable scanning of four different fluorescent dyes simultaneously with 2 scan heads, phosphor imaging, optical densitometry, chemiluminescence, and colorimetric analysis.

In some embodiments, one optical scan head will be used to detect multiple labels on a substrate. In some embodiments, a dual-band emission filter will enable detection of light of multiple wavelengths emitting from substrate. In some embodiments, two fluorescent wavelengths can be scanned simultaneously with one scan head. In some embodiments, a dual-band emission filter will allow phosphor emission and fluorescence emission to be detected with the same optical path and components. In some embodiments, more than one optical scan head will be used.

In some embodiments, multiple scan heads will allow for scanning several wavelengths at once. In some embodiments, 2 scan heads will be used to scan up to 4 channels (e.g., four different wavelengths) at once.

In some embodiments, the substrate will be placed on a scanning bed that is larger than the substrate. In some embodiments, a digital image will be taken of the scan bed and analyzed to define the boundaries of the substrate before scanning with optical scan head. In some embodiments, a digital image will be acquired using a charge-coupled device (CCD), a complementary metal-oxide semiconductor (CMOS), digital camera, or other appropriate digital imaging technology.

In some embodiments, multiple types of detectors will be used to optimize sensitivity. In some embodiments, a photomultiplier tube (PMT) will be used for wavelength range 300-700 nm, avalanche photodiode (APD) for 650-900 nm, and CCD for area, colorimetric, chemiluminescence from 400-900 nm.

In some embodiments, multiple types of light sources will be used. In some embodiments lasers and LEDs will be used to illuminate substrates.

In some embodiments, the present disclosure provides a detection instrument capable of distinguishing between at least two types of molecules in a single substrate, the detection instrument comprising: a first optical path comprising a laser light source and a first detector for scanning the substrate with light having a first wavelength; and a second optical path comprising an LED light source and a second detector for capturing an image of the substrate at visible wavelengths.

BRIEF DESCRIPTION OF THE DRAWINGS

FIG. 4 shows a scan head optic setup, and wavelength profile, capable of phosphorimaging or scanning 2 fluorescent dyes simultaneously, according to one embodiment of the present disclosure.

Figure 1:
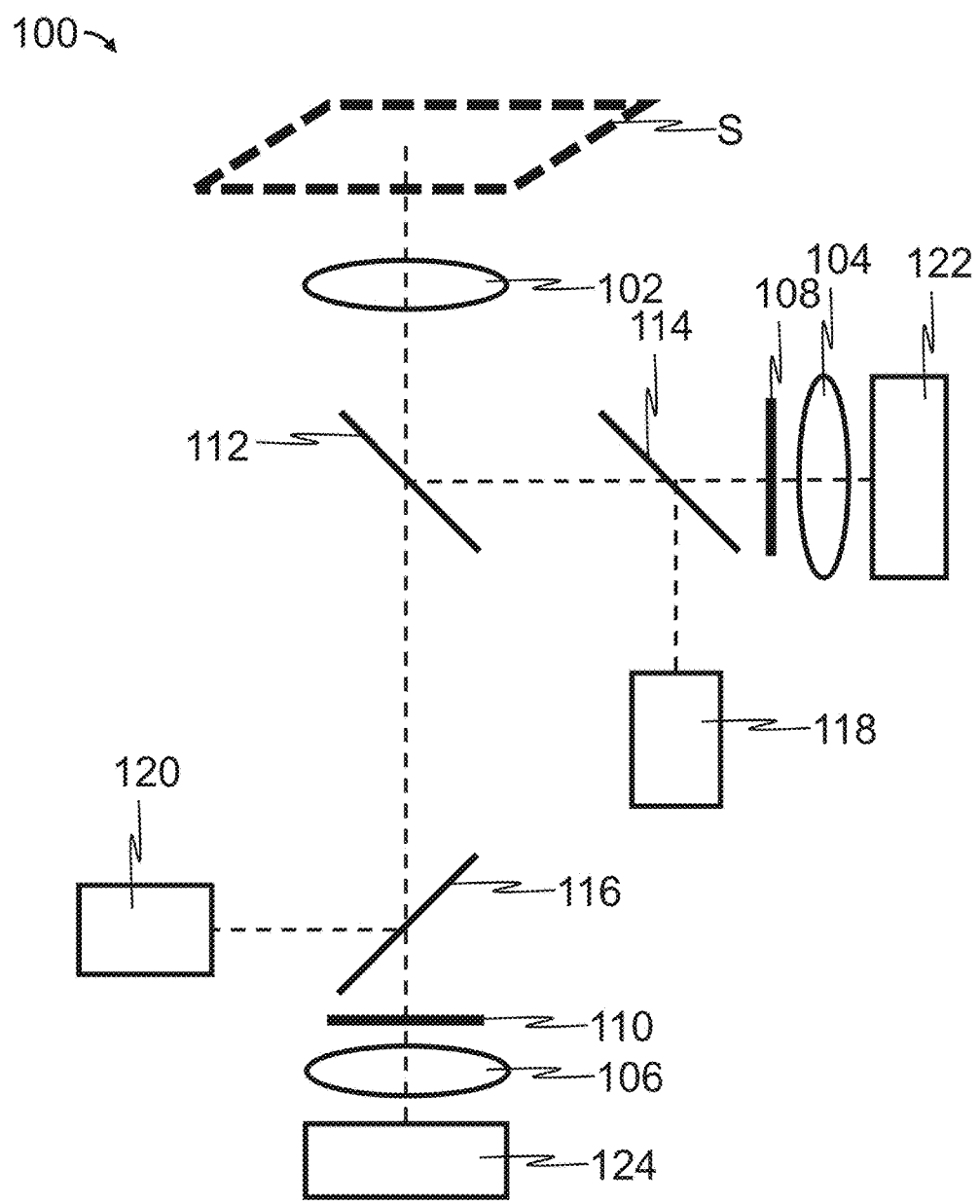
FIG. 1 shows a scan head optical path for simultaneous excitation and detection of two fluorescent labels according to one embodiment of the present disclosure.

The figures depict various embodiments of this disclosure for purposes of illustration only. One skilled in the art will readily recognize from the following discussion that alternative embodiments of the structures and methods illustrated herein may be employed without departing from the principles of embodiments described herein.

DETAILED DESCRIPTION

Biomolecule imaging instruments disclosed herein offer convenient multiplex imaging of biological substrates heretofore not possible using conventional substrate imaging technologies. In some embodiments, a biomolecule imaging instrument disclosed herein comprises a scanner and an large-area imager that, collectively, are capable of scanning and imaging a biological substrate that includes a plurality of differently-labeled biomolecules. In some embodiments, the biomolecule imaging instrument comprises a display for viewing a composite image comprising a plurality of individual images of a substrate, wherein each individual image includes visual information corresponding to a single type of labeled biomolecule.

In other embodiments, the instrument causes a separate display device to display a composite image comprising a plurality of individual images of a substrate, wherein each individual image includes visual information corresponding to a single type of labeled biomolecule. In some embodiments, each individual image is displayed in a single unique color in the displayed composite image.

The biomolecule imaging instruments disclosed herein are capable of distinguishing multiple types of labeled biomolecules. For example, in some embodiments, a biomolecule imaging instrument disclosed herein can distinguish between molecules labeled with two, three, or four types of biomolecules wherein each type of biomolecule is labeled with a different fluorescent tag.

In some embodiments, a biomolecule imaging instrument disclosed herein can distinguish between a first type of molecule in a substrate and a second type of molecule in the substrate. In some embodiments, the first type of molecule in the substrate is labeled with a fluorescent label, and the second type of molecule in the substrate is selected from the group consisting of: molecules labeled with a second, different fluorescent label, chemiluminescent molecules, colorimetric molecules, and phosphorescent molecules. In some embodiments, the first type of molecule in the substrate is a chemiluminescent molecule and the second type of molecule in the substrate is a colorimetric molecule or a phosphorescent molecule. In some embodiments, the first type of molecule is a colorimetric molecule and the second type of molecule is a phosphorescent molecule.

In some embodiments, a biomolecule imaging instrument disclosed herein can distinguish between a first type of molecule in a substrate, a second type of molecule in the substrate, and a third type of molecule in a substrate. In some embodiments, the first type of molecule is a molecule labeled with a first fluorescent label, the second type of molecule is a molecule labeled with a second, different fluorescent label, and the third type of molecule is a molecule labeled with a third, different fluorescent label. In some embodiments, the first type of molecule is a molecule labeled with a first fluorescent label, the second type of molecule is a molecule labeled with a second, different fluorescent label, and the third type of molecule is a chemiluminescent molecule. In some embodiments, the first type of molecule is a molecule labeled with a first fluorescent label, the second type of molecule is a molecule labeled with a second, different fluorescent label, and the third type of molecule is a colorimetric molecule. In some embodiments, the first type of molecule is a molecule labeled with a first fluorescent label, the second type of molecule is a molecule labeled with a second, different fluorescent label, and the third type of molecule is a phosphorescent molecule. In some embodiments, the first type of molecule is a molecule labeled with a fluorescent label, the second type of molecule is a chemiluminescent molecule, and the third type of molecule is a colorimetric molecule. In some embodiments, the first type of molecule is a molecule labeled with a fluorescent label, the second type of molecule is a chemiluminescent molecule, and the third type of molecule is a phosphorescent molecule. In some embodiments, the first type of molecule is a molecule labeled with a fluorescent label, the second type of molecule is a colorimetric molecule, and the third type of molecule is a phosphorescent molecule. In some embodiments, the first type of molecule is a chemiluminescent molecule, the second type of molecule is a colorimetric molecule, and the third type of molecule is a phosphorescent molecule.

In some embodiments, a biomolecule imaging instrument disclosed herein can distinguish between a first type of molecule in a substrate, a second type of molecule in the substrate, a third type of molecule in a substrate, and a fourth type of molecule in the substrate. In some embodiments, the first type of molecule is a molecule labeled with a first fluorescent label, the second type of molecule is a molecule labeled with a second, different fluorescent label, the third type of molecule is a molecule labeled with a third, different fluorescent label, and the fourth type of molecule is a molecule labeled with a fourth, different fluorescent label. In some embodiments, the first type of molecule is a molecule labeled with a first fluorescent label, the second type of molecule is a molecule labeled with a second, different fluorescent label, the third type of molecule is a molecule labeled with a third, different fluorescent label, and the fourth type of molecule is a colorimetric molecule. In some embodiments, the first type of molecule is a molecule labeled with a first fluorescent label, the second type of molecule is a molecule labeled with a second, different fluorescent label, the third type of molecule is a molecule labeled with a third, different fluorescent label, and the fourth type of molecule is a phosphorescent molecule. In some embodiments, the first type of molecule is a molecule labeled with a first fluorescent label, the second type of molecule is a molecule labeled with a second, different fluorescent label, the third type of molecule is a chemiluminescent molecule, and the fourth type of molecule is a colorimetric molecule. In some embodiments, the first type of molecule is a molecule labeled with a first fluorescent label, the second type of molecule is a molecule labeled with a second, different fluorescent label, the third type of molecule is a chemiluminescent molecule, and the fourth type of molecule is a phosphorescent molecule. In some embodiments, the first type of molecule is a molecule labeled with a fluorescent label, the second type of molecule is a chemiluminescent molecule, the third type of molecule is a colorimetric molecule, and the fourth type of molecule is a phosphorescent molecule.

In some embodiments, a biomolecule imaging instrument disclosed herein can distinguish between a first type of molecule in a substrate, a second type of molecule in the substrate, a third type of molecule in a substrate, a fourth type of molecule in the substrate, and a fifth type of molecule in the substrate. In some embodiments, the first type of molecule is a molecule labeled with a first fluorescent label, the second type of molecule is a molecule labeled with a second, different fluorescent label, the third type of molecule is a molecule labeled with a third, different fluorescent label, the fourth type of molecule is a molecule labeled with a fourth, different fluorescent label, and the fifth type of molecule is a chemiluminescent molecule. In some embodiments, the first type of molecule is a molecule labeled with a first fluorescent label, the second type of molecule is a molecule labeled with a second, different fluorescent label, the third type of molecule is a molecule labeled with a third, different fluorescent label, the fourth type of molecule is a molecule labeled with a fourth, different fluorescent label, and the fifth type of molecule is a colorimetric molecule. In some embodiments, the first type of molecule is a molecule labeled with a first fluorescent label, the second type of molecule is a molecule labeled with a second, different fluorescent label, the third type of molecule is a molecule labeled with a third, different fluorescent label, the fourth type of molecule is a molecule labeled with a fourth, different fluorescent label, and the fifth type of molecule is a phosphorescent molecule.

In some embodiments, a biomolecule imaging instrument disclosed herein can distinguish between a first type of molecule in a substrate, a second type of molecule in the substrate, a third type of molecule in a substrate, a fourth type of molecule in the substrate, a fifth type of molecule in the substrate, and a sixth type of molecule in the substrate. In some embodiments, the first type of molecule is a molecule labeled with a first fluorescent label, the second type of molecule is a molecule labeled with a second, different fluorescent label, the third type of molecule is a molecule labeled with a third, different fluorescent label, the fourth type of molecule is a molecule labeled with a fourth, different fluorescent label, the fifth type of molecule is a chemiluminescent molecule, and the sixth type of molecule is a colorimetric molecule. In some embodiments, the first type of molecule is a molecule labeled with a first fluorescent label, the second type of molecule is a molecule labeled with a second, different fluorescent label, the third type of molecule is a molecule labeled with a third, different fluorescent label, the fourth type of molecule is a molecule labeled with a fourth, different fluorescent label, the fifth type of molecule is a chemiluminescent molecule, and the sixth type of molecule is a phosphorescent molecule. In some embodiments, the first type of molecule is a molecule labeled with a first fluorescent label, the second type of molecule is a molecule labeled with a second, different fluorescent label, the third type of molecule is a molecule labeled with a third, different fluorescent label, the fourth type of molecule is a molecule labeled with a fourth, different fluorescent label, the fifth type of molecule is a colorimetric molecule, and the sixth type of molecule is a phosphorescent molecule.

In some embodiments, a biomolecule imaging instrument disclosed herein can distinguish between a first type of molecule in a substrate, a second type of molecule in the substrate, a third type of molecule in a substrate, a fourth type of molecule in the substrate, a fifth type of molecule in the substrate, a sixth type of molecule in the substrate, and a seventh type of molecule in the substrate. In some embodiments, the first type of molecule is a molecule labeled with a first fluorescent label, the second type of molecule is a molecule labeled with a second, different fluorescent label, the third type of molecule is a molecule labeled with a third, different fluorescent label, the fourth type of molecule is a molecule labeled with a fourth, different fluorescent label, the fifth type of molecule is a chemiluminescent molecule, the sixth type of molecule is a colorimetric molecule, and the seventh type of molecule is a phosphorescent molecule.

FIG. 1 discloses a representative diagram of the optical path for detection of biomolecules by a scan head. In a typical mode of using the scan head, a substrate S is scanned using the optical scan head 100. Light from light source 118, is reflected off beam splitter 114, and then beam splitter 112, before being focused through objective 102, onto substrate S. In the case where the substrate is labeled with a fluorescent molecule, the fluorescent molecule is excited by the laser light, and fluoresces, emitting light of a different wavelength than the laser. This light can pass through objective 102, be reflected by beam splitter 112, and then pass-through beam splitter 114, which is selected to reflect light of the laser wavelength, and allow light of the fluorescent emission wavelength to pass through. An emission filter 108 is used to eliminate light not coming from the intended fluorophore. In some embodiments, the emission filter 108 is a dual-band emission filter that eliminates light not coming from either of two intended fluorophores. Lastly, the fluorescent emission light (e.g., one or two fluorescent wavelengths of light) is focused through focusing lens 104 onto detector 122.

Likewise, a second fluorophore can be read with the same scan head by light from a second light source 120, reflecting off beam splitter 116, and passing through beam splitter 112 before being focused through objective 102 and exciting a second fluorophore on substrate S. Light emitted from this second fluorophore will pass through the objective 102, pass through beam splitter 112 and beam splitter 116 before finally passing through emission filter 110, focusing lens 106 and onto detector 124.

By selecting appropriate beam splitters 112, 114, and 116 two fluorophores may be read simultaneously using one scanning head. In some embodiments, the optical paths for two fluorophores have minimal overlap in emission spectra so cross-talk between the emitted fluorescent light wavelengths is minimized.

Figures 2, 3:
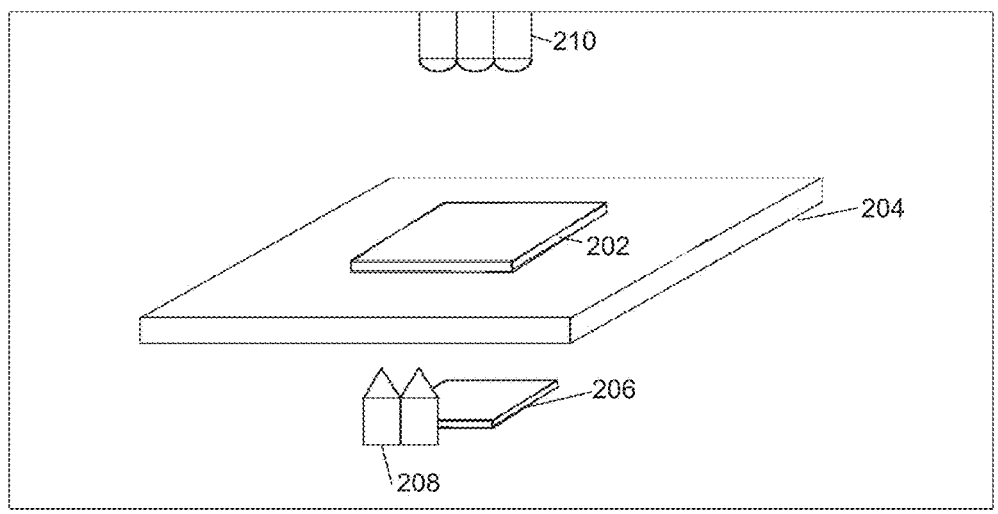
FIG. 2 shows a schematic of a scanning device consistent with one embodiment of the present disclosure.
FIG. 3 shows a scan head optic setup, and wavelength profile, capable of scanning 2 fluorescent dyes simultaneously, according to one embodiment of the present disclosure.

FIG. 2 discloses a representative diagram of a biomolecule scanner 200. A substrate, 202, is placed onto the scan bed 204. The substrate can be interrogated several different ways. The CCD 206 can be used to image the substrate using a particular color of LED 210 (colorimetric/optical densitometry), in darkness (chemiluminescence) or in white or colored light to establish substrate position on bed before scanning. The dual scan head 208 shown can scan 4 different fluorescent dyes simultaneously, or can be used for scanning a phosphorimaging screen. In some embodiments, the CCD 206 is used to identify a region of interest within the area of the scan bed 204 that requires scanning. For example, in some embodiments, the CCD 206 captures an image (e.g., a low-resolution image) of the entire scan bed 204, and an associated processor identifies a smaller region of the scan bed 204 that is emitting light or reflecting light from the LED 210. The dual scan head 208 then performs a scan of the identified smaller region of the scan bed 204.

FIG. 3 provides a representative example of selecting filters, beam splitters, light sources and detectors to enable two color scanning in a single optical scan head. In this case, components were selected to scan "green excitable" dyes, which can be excited by a 525 nm light source and emit light at a wavelength between 555 to 585 nm, and near-infra-red dyes ("NIR excitable") which can be excited by a 780 nm light source and emit light at a wavelength between 805 to 855 nm. Optical components can of course be selected to allow detection of any two fluorophores which do not overlap in excitation or emission wavelength.

FIG. 4 provides a representative example of selecting filters, beam splitters, light sources and detectors to enable both phosphor imaging and two color scanning in a single optical scan head. In this case, components were selected to scan "red excitable" dyes, which can be excited by a 635 nm light source and emit light at a wavelength between 675 to 735 nm, and "blue excitable" dyes which can be excited by a 473 nm light source and emit light at a wavelength between 495 to 525 nm. By selecting appropriate filters and beam splitters, this same optical head can be used to read phosphorimaging plates which can be excited using an 635 nm light source and emit light at a wavelength between 370 and 410 nm.

Figure 5:
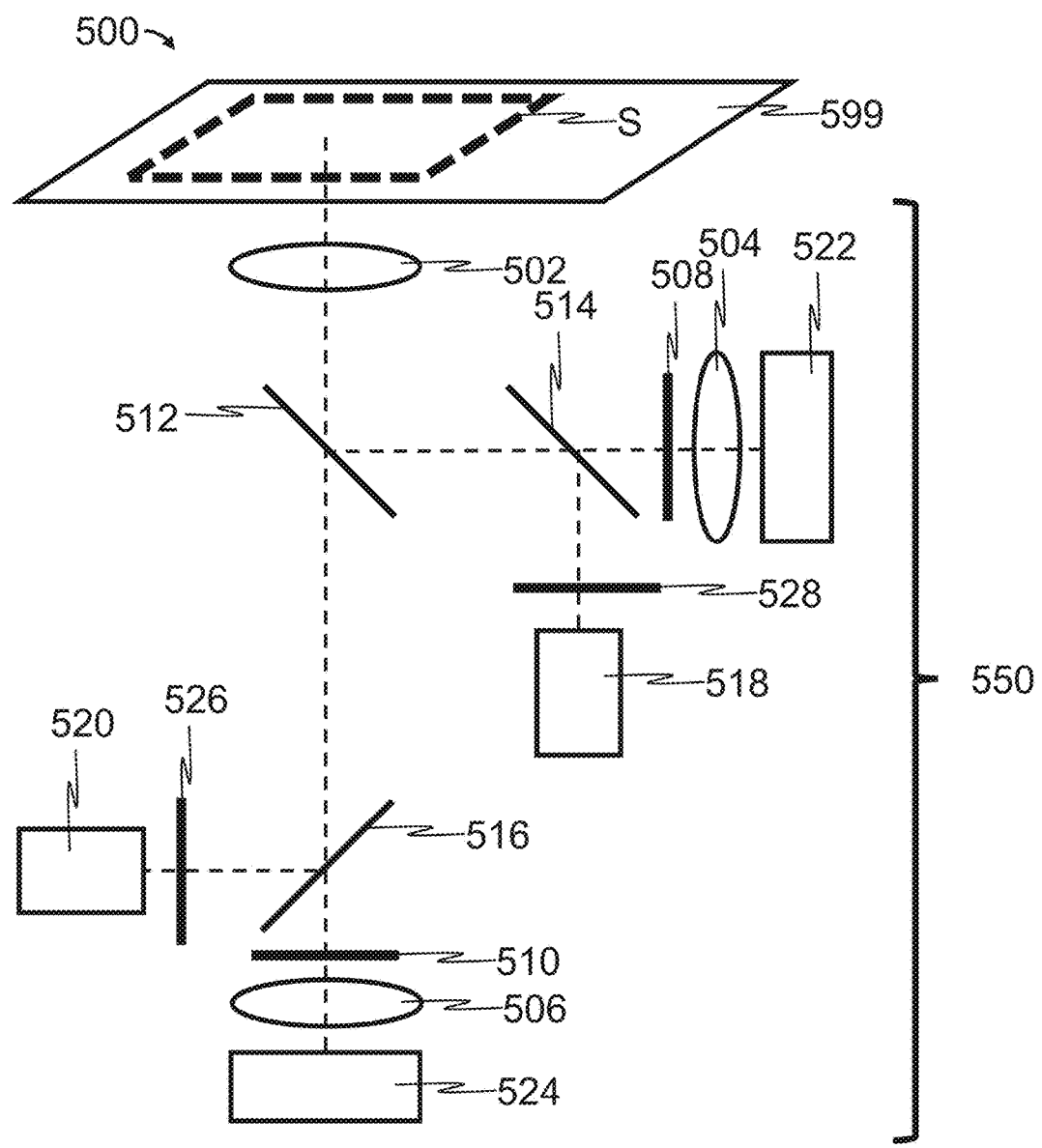
FIG. 5 shows a scan head optical path for simultaneous excitation and detection of two fluorescent labels according to one embodiment of the present disclosure.

FIG. 5 discloses a representative diagram of the optical path for detection of biomolecules by a scan head 550. In a typical mode of using the scan head 550, a substrate S is scanned by light from light source 518, which may pass through a cleanup filter 528, reflect off beam splitter 514, and then beam splitter 512, before being focused through objective 502, onto substrate S. In the case where the substrate is labeled with a fluorescent molecule, the fluorescent molecule is excited by the laser light, and fluoresces, emitting light of a different wavelength than the laser. This light can pass through objective 502, be reflected by beam splitter 512, and then pass-through beam splitter 514, which is selected to reflect light of the laser wavelength, and allow light of the fluorescent emission wavelength to pass through. An emission filter 508 is used to eliminate light not coming from the intended fluorophore. Lastly, the fluorescent emission light is focused through focusing lens 504 onto detector 522.

Likewise, a second fluorophore can be read with the same scan head by light from a second light source 520, which passes through a cleanup filter 526 reflects off beam splitter 516, and passes through beam splitter 512 before being focused through objective 502 and exciting a second fluorophore on substrate 501. Light emitted from this second fluorophore will pass through the objective 502, pass through beam splitter 512 and beam splitter 516 before finally passing through emission filter 510, focusing lens 506 and onto detector 524.

By selecting appropriate beam splitters 512, 514, and 516 two fluorophores may be read simultaneously using one scanning head. By designing the optical path for two fluorophores that have minimal overlap in emission spectrum, cross-talk will be minimized.

In some embodiments, light source 518 is a laser that emits light at 520 nm (e.g., PL-520, OSRAM Opto Semiconductors GmbH), and light source 520 is a laser that emits light at 784 nm (e.g., GH0781RA2c, Sharp). In such embodiments, the objective 502 may have a focus length of 20 mm (e.g., GCL-010612, Daheng). In such embodiments, the dichroic beam splitter 516 may be a single-edge laser-flat dichroic beamsplitter (e.g., Di02-R785, Semrock), the dichroic beam splitter 514 may be a single-edge laser-flat dichroic beamsplitter (e.g., FF552-Di02, Semrock), and the dichroic beam splitter 512 may be a single-edge laser-flat dichroic beamsplitter (e.g., FF757-Di01, Semrock). The cleanup filter 528 may be a single-band bandpass filter (e.g., FF01-514/30, Semrock), while cleanup filter 526 may be a single-band bandpass filter (e.g., FF01-769/41, Semrock). Emission filter 508 may be a single-band bandpass filter (e.g., FF01-565/24, Semrock), while emission filter 510 may be a single-band bandpass filter (e.g., FF01-832/37, Semrock). Detector 522 in such embodiments, may be an avalanche photodiode (e.g., S12023-10, Hamamatsu), while detector 524 may be an avalanche photodiode that is the same or different than detector 522 (e.g., S12023-10, Hamamatsu). Focus lens 504, 506 may be a plano-convex lens having a focal length of 50 mm (e.g., GCL-010107, Daheng). The scan bed 599 may be a glass scan bed of suitable thickness, such as 5 mm (e.g., BK7 glass, Glass Dynamics LLC).

In some embodiments, light source 518 is a laser that emits light at 520 nm (e.g., PL-520, OSRAM Opto Semiconductors GmbH), and light source 520 is a laser that emits light at 658 nm (e.g., ML101J25, Mitsubishi). In such embodiments, the objective 502 may have a focus length of 20 mm (e.g., GCL-010612, Daheng). In such embodiments, the dichroic beam splitter 516 may be a single-edge laser-flat dichroic beamsplitter (e.g., FF677-Di01, Semrock), the dichroic beam splitter 514 may be a single-edge laser-flat dichroic beamsplitter (e.g., BCOME-0015, Semrock), and the dichroic beam splitter 512 may be a single-edge laser-flat dichroic beamsplitter (e.g., FF593-Di03, Semrock). The cleanup filter 528 may be a single-band bandpass filter (e.g., FF01-475/28, Semrock), while cleanup filter 526 may be a single-band bandpass filter (e.g., 658 nm short pass, Filtech Photonics). Emission filter 508 may be a single-band bandpass filter (e.g., BCOME-0016, Semrock), while emission filter 510 may be a single-band bandpass filter (e.g., FF01-710/40, Semrock). Detector 522 in such embodiments, may be a photomultiplier tube (e.g., H10721-110, Hamamatsu), while detector 524 may be an avalanche photodiode (e.g., S12023-10, Hamamatsu). Focus lenses 504,506 may be a plano-convex lens having a focal length of 50 mm (e.g., GCL-010107, Daheng). The scan bed 599 may be a glass scan bed of suitable thickness, such as 5 mm (e.g., BK7 glass, Glass Dynamics LLC).

Figure 6:
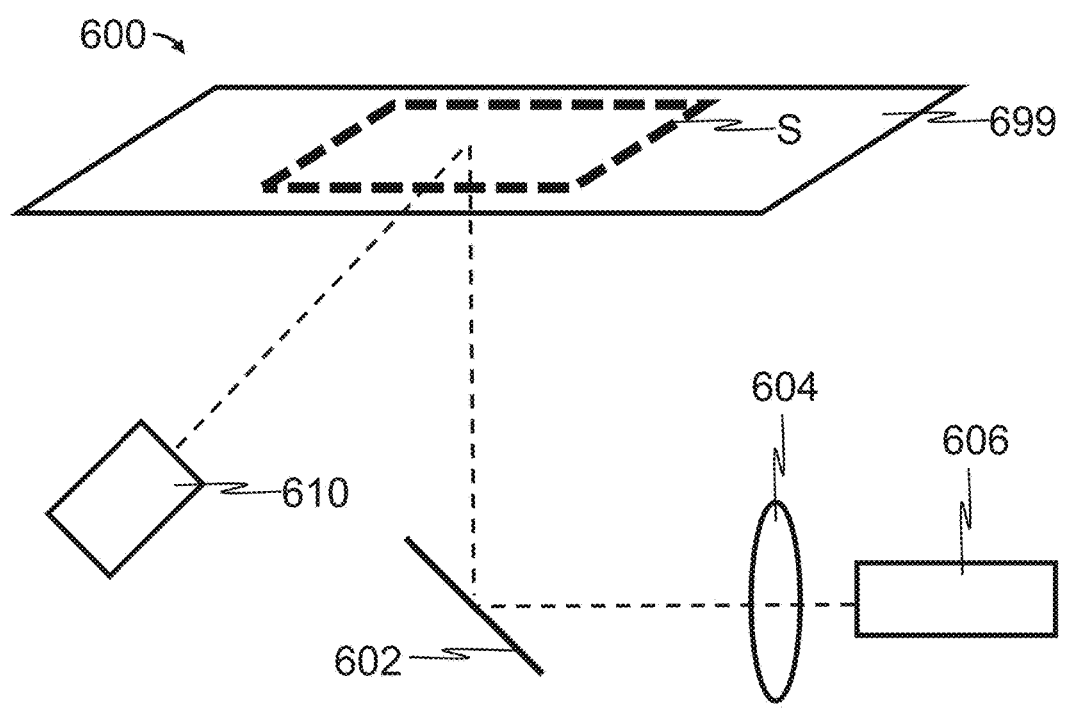
FIG. 6 shows a scan head optical path for illumination by LED and detection by CCD camera of a substrate placed on a glass bed according to one embodiment of the present disclosure.

Referring now to FIG. 6, a biomolecule scanner 600 consistent with the present disclosure comprises a scan bed 699, an LED light source 610, mirror 602, a lens 604, and a CCD camera 606. A substrate, S, is placed onto the scan bed 699. LED light emitted by the LED light source 610 penetrates the scan bed 699 to illuminate the substrate S. The LED light reflected from the substrate S then reflects off of the mirror 602. The lens 604 focuses the reflected light to the CCD camera 606 for capture. The biomolecule scanner 600 can be used to image the substrate S using a particular color of LED 610 (colorimetric/optical densitometry), in darkness (chemiluminescence) or in white or colored light to establish substrate position on bed before scanning. In some embodiments, the lens 604 has a focal length of 25 mm and maximum aperture of f/0.95 (e.g., Nokton 25 mm, f/0.95, Voigtlander), and the camera 606 is configured to capture at least 4 million pixels per scan, such as at least 4 million pixels, at least 5 million pixels, or at least 6 million pixels per image. In some embodiments, the CCD camera 606 is used to identify a region of interest within the area of the scan bed 699 that requires scanning. For example, in some embodiments, the CCD camera 606 captures an image (e.g., a low-resolution image) of the entire scan bed 699, and an associated processor identifies a smaller region of the scan bed 699 that is emitting light or reflecting light from the LED 610. The biomolecule scanner 600 then performs a scan of the identified smaller region of the scan bed 699.

Figure 7A:
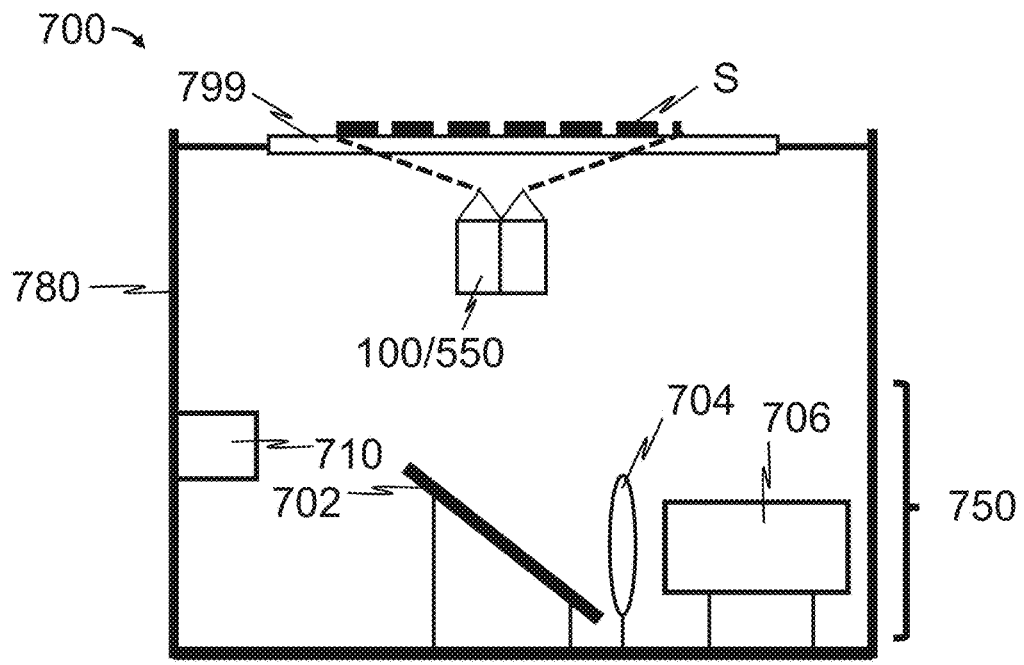
FIG. 7A shows a schematic view of a scanning instrument comprising an LED-illuminated CCD camera and at least one laser-illuminated scan head consistent with one embodiment of the present disclosure.
Figure 7B:
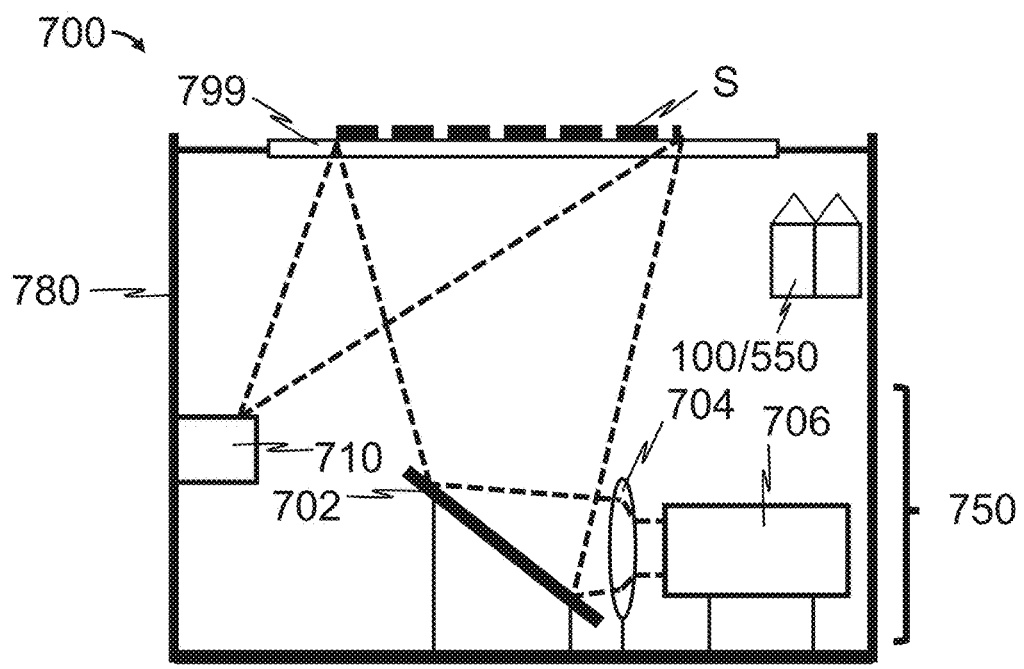
FIG. 7B shows a schematic view of the scanning instrument of FIG. 7A wherein the at least one laser-illuminated scan head has been retracted to enable imaging by the LED-illuminated CCD camera.

As shown representatively in FIGS. 7A-7B, the present disclosure provides a scanning instrument 700 comprising one or more laser-illuminated scan heads 100/550, an LED-illuminated Camera 750, a transparent scan bed 799, and an enclosure 780. In some embodiments, the one or more laser-illuminated scan heads 100/550 is consistent with optical scan head 100 described above and shown representatively in FIG. 1. In other embodiments, the one or more laser-illuminated scan heads 100/550 is consistent with optical scan head 550 described above and shown representatively in FIG. 5.

In some embodiments, the LED-illuminated camera head 750 comprises an LED light source 710, a mirror 702, a camera lens 704, and a camera 706. In operation, the one or more laser-illuminated scan heads 100/550 is moved in line with the substrate S, as shown in FIG. 7A. The substrate S is then scanned with the one or more laser-illuminated scan heads 100/500 as described above with respect to FIG. 1 or FIG. 5. Once the one or more laser scan heads 100/550 have completed scanning the substrate S, the one or more laser scan heads 100/550 is moved out of line with the substrate S as shown in FIG. 7B, so that LED light from the LED light source 710 is not blocked by the one or more laser-illuminated scan heads 100/550.

Scanning of the substrate S by the LED camera head 750 then proceeds. LED light emitted by the LED light source 710 penetrates the scan bed 799 to illuminate the substrate S. The LED light reflected from the substrate S then reflects off of the mirror 702. The lens 704 focuses the reflected light to the CCD camera 706 for capture. In this mode, the scanning instrument 700 can be used to image the substrate S using a particular color of LED 710 (colorimetric/optical densitometry), in darkness (chemiluminescence) or in white or colored light to establish substrate position on bed before scanning. In some embodiments, the lens 704 has a focal length of 25 mm and maximum aperture of f/0.95 (e.g., Nokton 25 mm, f/0.95, Voigtlander), and the camera 706 is configured to capture at least 4 million pixels per scan, such as at least 4 million pixels, at least 5 million pixels, or at least 6 million pixels per scan.

In other embodiments, scanning of the substrate S by the LED scan head 750 occurs first, followed by scanning by the one or more laser-illuminated scan heads 100/550. In such embodiments, the one or more laser-illuminated scan heads 100/550 is moved out of line with the substrate S as shown in FIG. 7B, so that LED light from the LED light source 710 is not blocked by the one or more laser-illuminated scan heads 100/550. LED light emitted by the LED light source 710 penetrates the scan bed 799 to illuminate the substrate S. The LED light reflected from the substrate S then reflects off of the mirror 702. The lens 704 focuses the reflected light to the CCD camera 706 for capture. In this mode, the scanning instrument 700 can be used to image the substrate S using a particular color of LED 710 (colorimetric/optical densitometry), in darkness (chemiluminescence) or in white or colored light to establish substrate position on bed before scanning. In some embodiments, the lens 704 has a focal length of 25 mm and maximum aperture of f/0.95 (e.g., Nokton 25 mm, f/0.95, Voigtlander), and the camera 706 is configured to capture at least 4 million pixels per scan, such as at least 4 million pixels, at least 5 million pixels, or at least 6 million pixels per scan.

Thereafter, the LED light source 710 is turned off, and scanning of the substrate S by the one or more laser-illuminated scan heads 100/550 proceeds. The one or more laser-illuminated scan heads 100/550 is moved in line with the substrate S, as shown in FIG. 7A. The substrate S is then scanned with the one or more laser-illuminated scan heads 100/500 as described above with respect to FIG. 1 or FIG. 5.

In some embodiments, a method of imaging a biological sample comprises placing the sample on a scanning bed of an imaging instrument consistent with the present disclosure, illuminating the biological sample with a first light having a first wavelength, capturing a first light emitted from the biological sample, illuminating the biological sample with a second light having a second wavelength, and capturing a second light emitted from the biological sample, wherein the biological sample is not moved after capturing the first light emitted from the biological sample and before illuminating the biological sample with the second light. In some embodiments, the method further comprises combining a pattern from the first captured light with a pattern from the second captured light to form a composite image.

In some embodiments, a method of imaging a biological sample comprises placing the sample on a scanning bed of an imaging instrument consistent with the present disclosure, illuminating the biological sample with a first light having a first wavelength, capturing a first light emitted from the biological sample, illuminating the biological sample with a second light having a second wavelength, capturing a second light emitted from the biological sample, illuminating the biological sample with a third light having a third wavelength, and capturing a third light emitted from the biological sample, wherein the biological sample is not moved after capturing the first light emitted from the biological sample and before illuminating the biological sample with the second light, and wherein the biological sample is not moved after capturing the second light emitted from the biological sample and before illuminating the biological sample with the third light. In some embodiments, the method further comprises combining a pattern from the first captured light with a pattern from the second captured light and with a pattern from the third captured light to form a composite image.

In some embodiments, a method of imaging a biological sample comprises placing the sample on a scanning bed of an imaging instrument consistent with the present disclosure, illuminating the biological sample with a first light having a first wavelength, capturing a first light emitted from the biological sample, illuminating the biological sample with a second light having a second wavelength, capturing a second light emitted from the biological sample, illuminating the biological sample with a third light having a third wavelength, capturing a third light emitted from the biological sample, illuminating the biological sample with a fourth light having a fourth wavelength, and capturing a fourth light emitted from the biological sample, wherein the biological sample is not moved after capturing the first light emitted from the biological sample and before illuminating the biological sample with the second light, wherein the biological sample is not moved after capturing the second light emitted from the biological sample and before illuminating the biological sample with the third light, and wherein the biological sample is not moved after capturing the third light emitted from the biological sample and before illuminating the biologicals sample with the fourth light. In some embodiments, the method further comprises combining a pattern from the first captured light with a pattern from the second captured light, with a pattern from the third captured light, and with a pattern from the fourth captured light to form a composite image.

In some embodiments, the present disclosure provides a composite image comprising a first pattern having a first color and a second pattern having a second color, wherein the first pattern corresponds to a pattern of first labeled biomolecules present in a 2D or 3D biological sample, and wherein the second pattern corresponds to a pattern of second labeled biomolecules present in the 2D or 3D biological sample, wherein the first labeled biomolecules and the second labeled biomolecules are different. In some embodiments, the first labeled biomolecules are excitable at a first wavelength of light and the second labeled biomolecules are excitable at a second, different wavelength of light. The images shown in FIGS. 8A, 8B, 8C, 8I, 8K, 8L and 8N are each consistent with such embodiments.

Figure 8A:
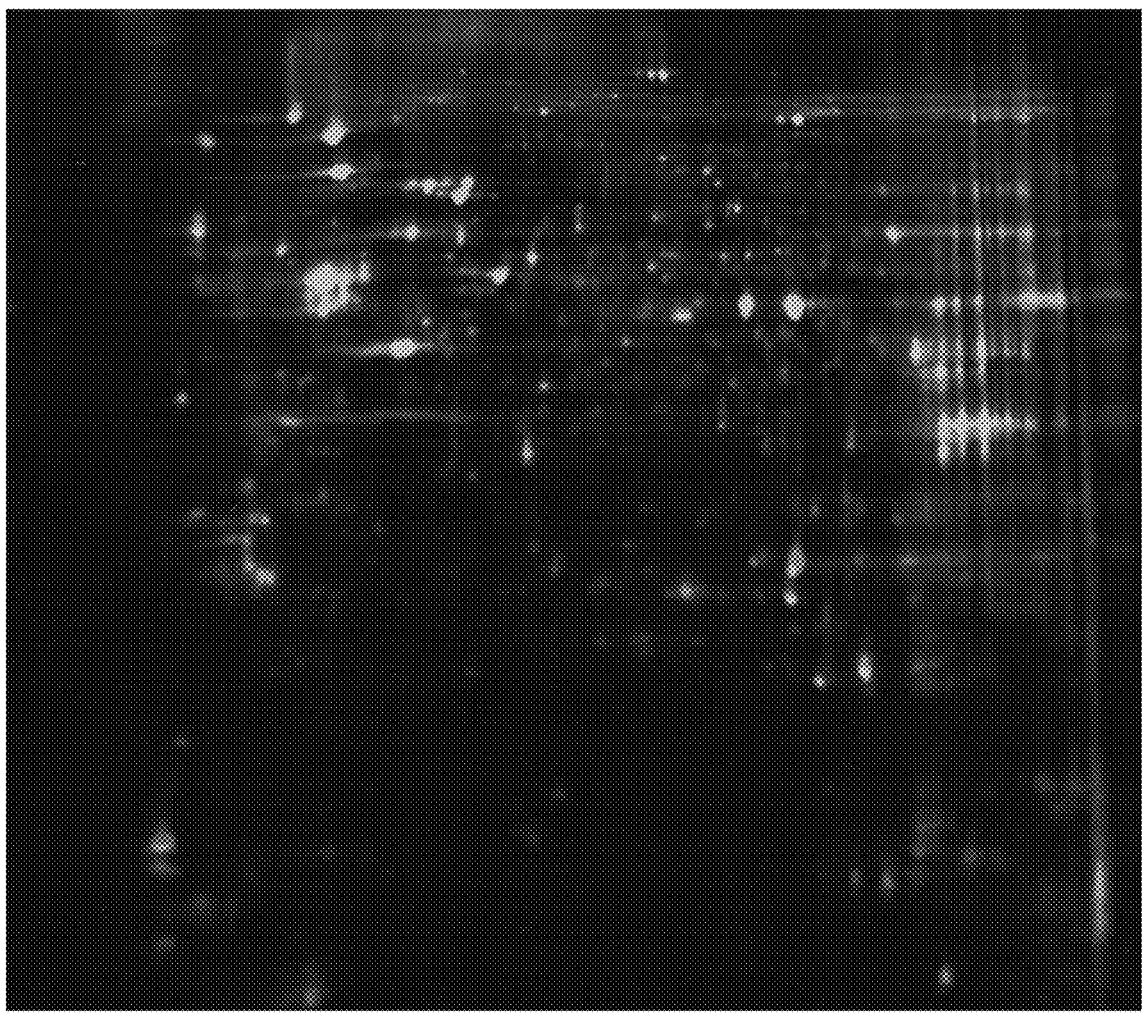
FIG. 8A shows an image obtained from simultaneous detection of two fluorescent dyes (Cy3 and Cy5) from a two-dimensional electrophoresis gel consistent with one embodiment of the present disclosure.
Figure 8B:
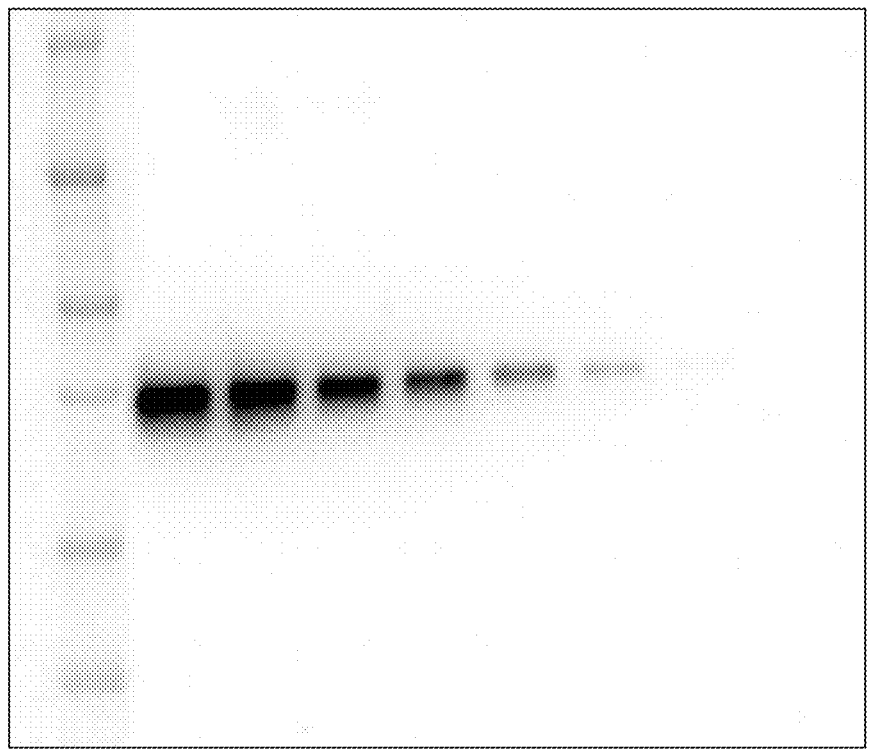
FIG. 8B shows an image obtained from simultaneous detection of chemiluminescent and markers from an electrophoresis gel consistent with one embodiment of the present disclosure.
Figure 8C:
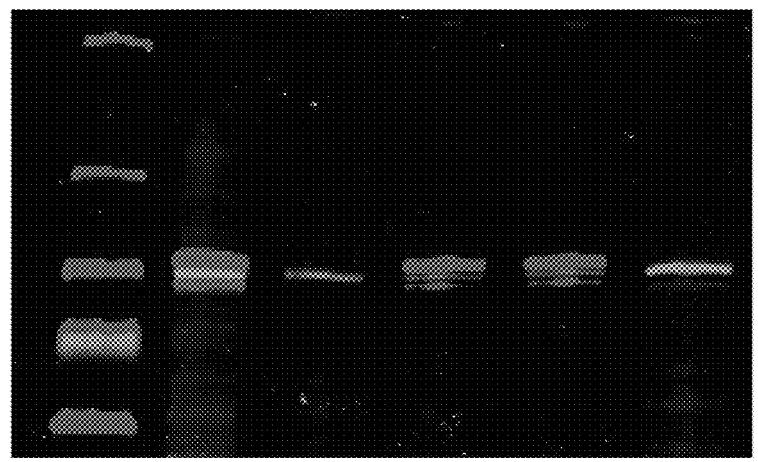
FIG. 8C shows an image obtained from simultaneous detection of two NIR dyes, one detectable at 700 nm and the other detectable at 800 nm, from a Western blot consistent with one embodiment of the present disclosure.
Figure 8D:
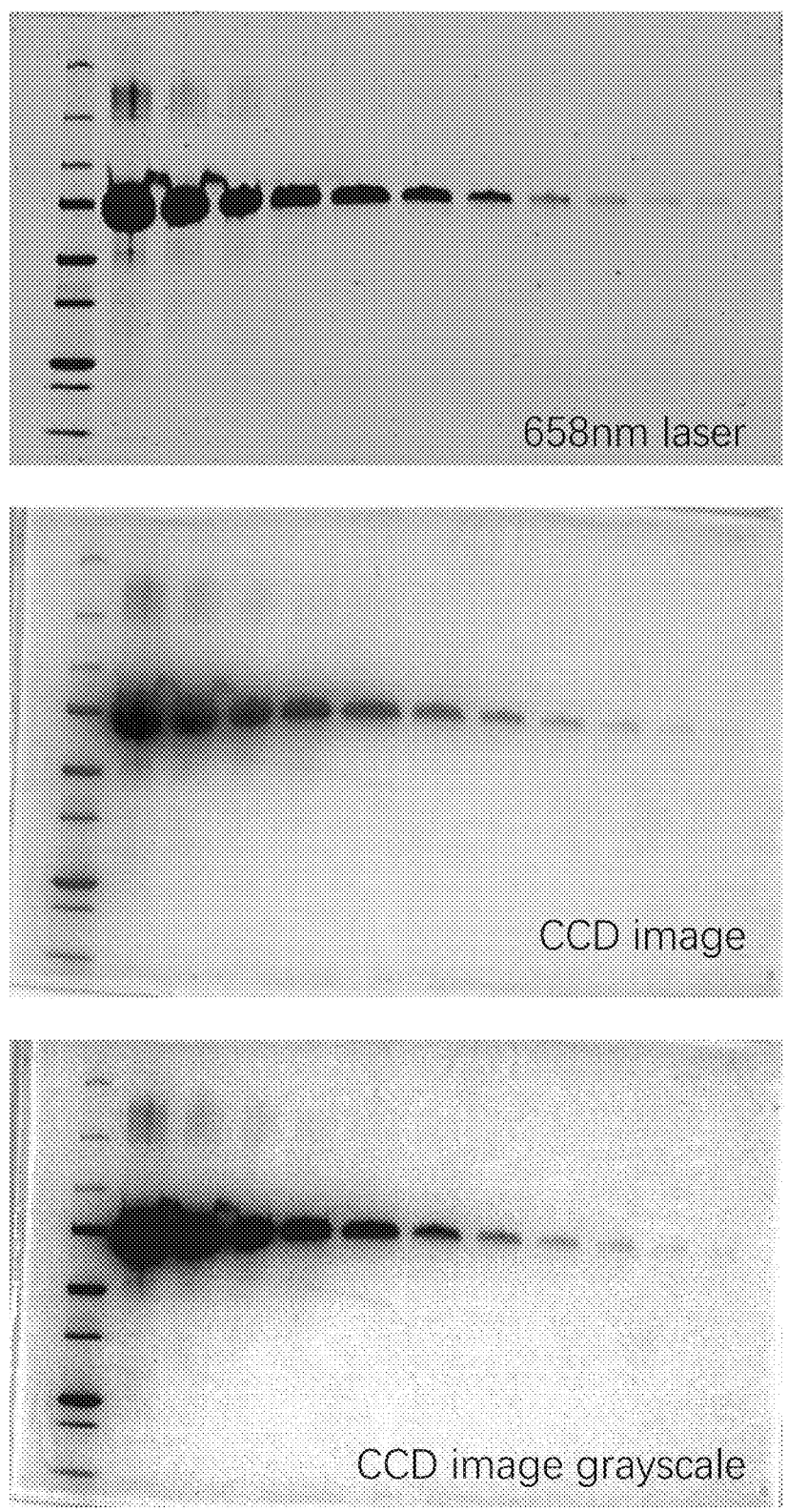
FIG. 8D shows images obtained from detection of Coomassie dye from an electrophoresis gel consistent with one embodiment of the present disclosure.
Figure 8E:
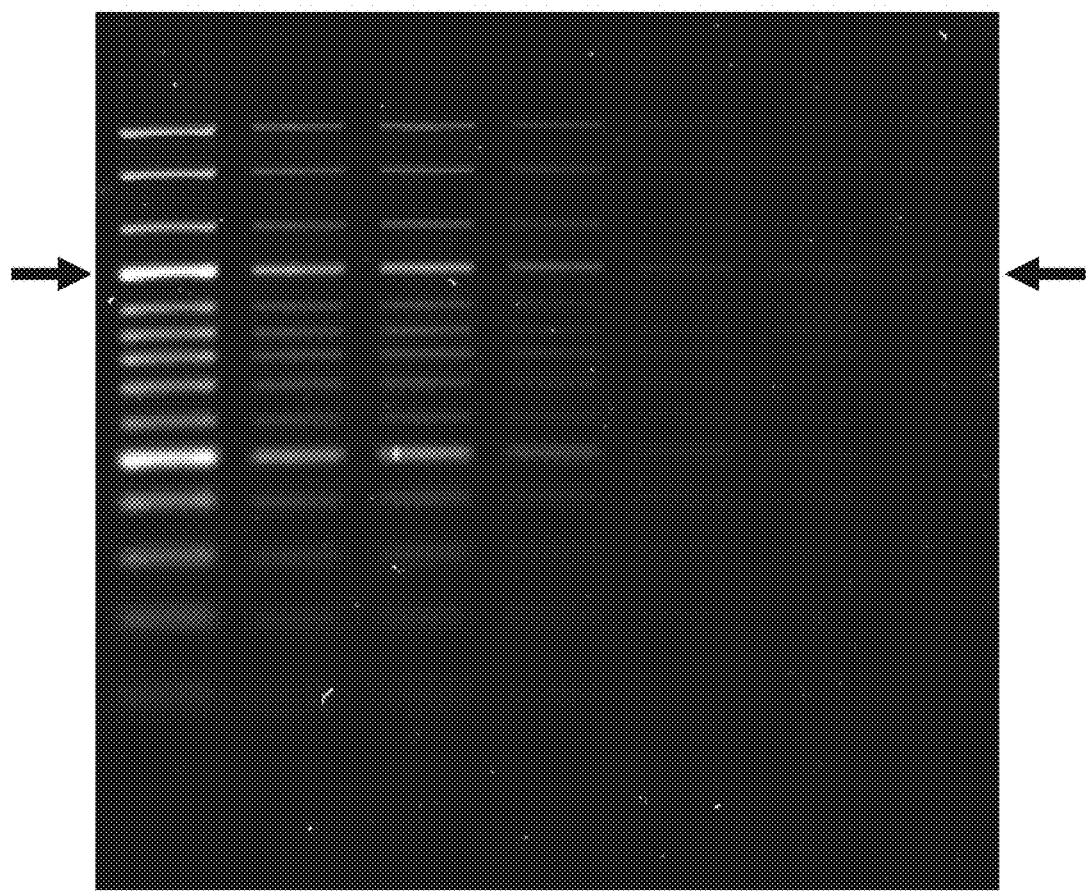
FIG. 8E shows an image obtained from detection of ethidium bromide dye from a DNA gel consistent with one embodiment of the present disclosure.
Figure 8F:
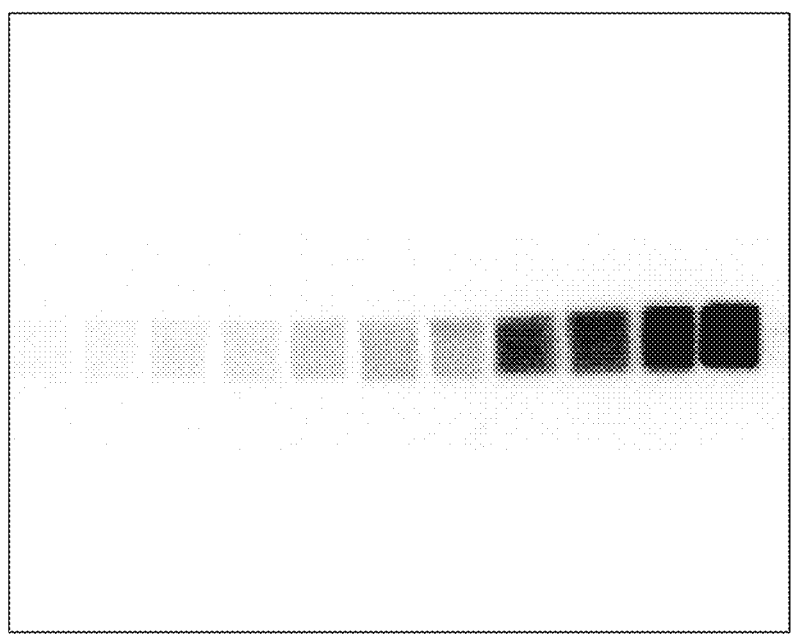
FIG. 8F shows an image obtained from detection of phosphorimaging dye from an electrophoresis gel consistent with one embodiment of the present disclosure.
Figure 8G:
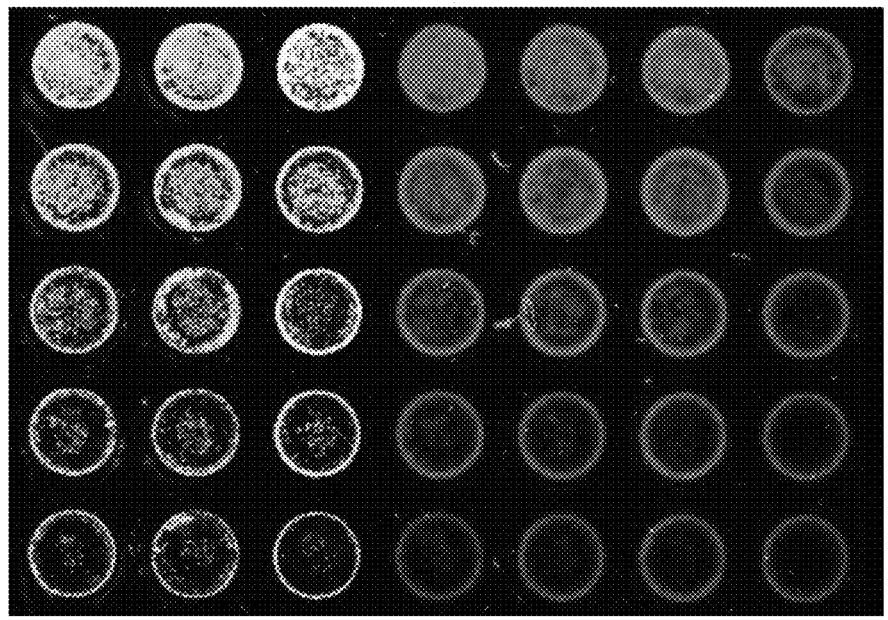
FIG. 8G shows an image obtained from simultaneous detection of three fluorescent dyes, one detectable at 520 nm, one detectable at 658 nm, and one detectable at 785 nm, from an in-cell Western gel consistent with one embodiment of the present disclosure.
Figure 8H:
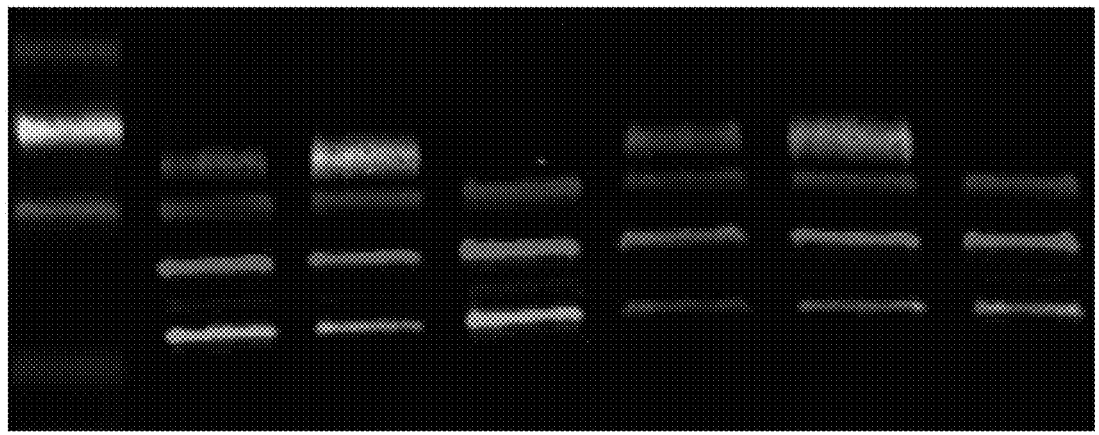
FIG. 8H shows an image obtained from simultaneous detection of four fluorescent dyes from a Western blot gel consistent with one embodiment of the present disclosure.
Figure 8I:
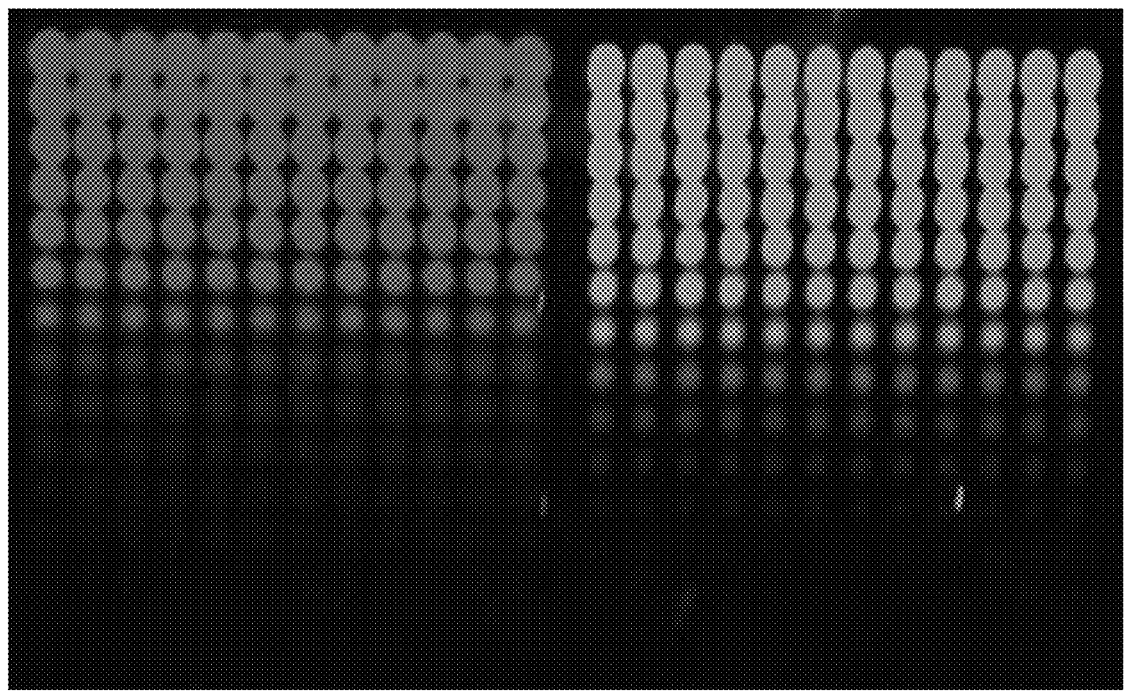
FIG. 8I shows an image obtained from simultaneous detection of two fluorescent dyes, one detectable at 520 nm and one detectable at 658 nm, from a microarray consistent with one embodiment of the present disclosure.
Figure 8J:
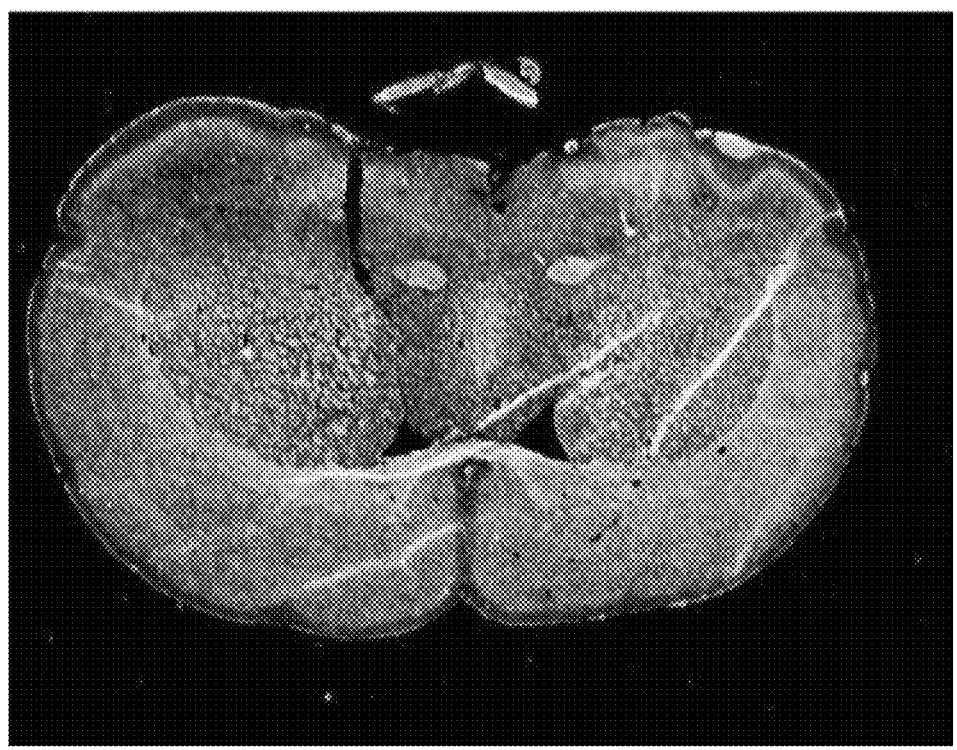
FIG. 8J shows an image obtained from simultaneous detection of three tissue dyes from a rat brain cross-sectional sample consistent with one embodiment of the present disclosure.
Figure 8K:
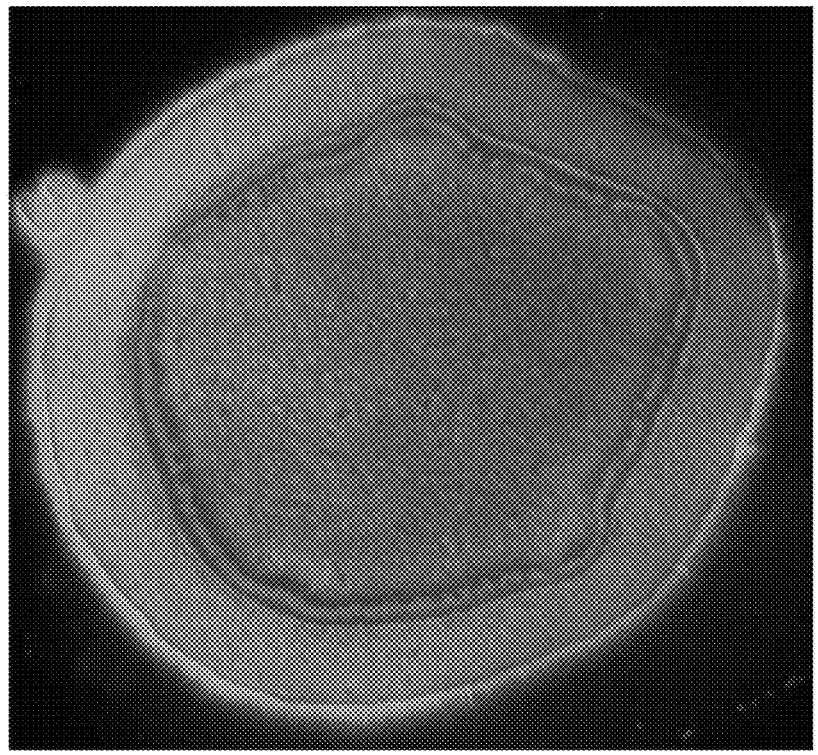
FIG. 8K shows an image obtained from simultaneous detection of two tissue dyes from a pelagorium stem cross-sectional sample consistent with one embodiment of the present disclosure.
Figure 8L:
FIG. 8L shows an image obtained from simultaneous detection of two fluorescent dyes, one detectable at 488 nm and the other detectable at 785 nm, from a bee head sample according to one embodiment of the present disclosure.
Figure 8M:
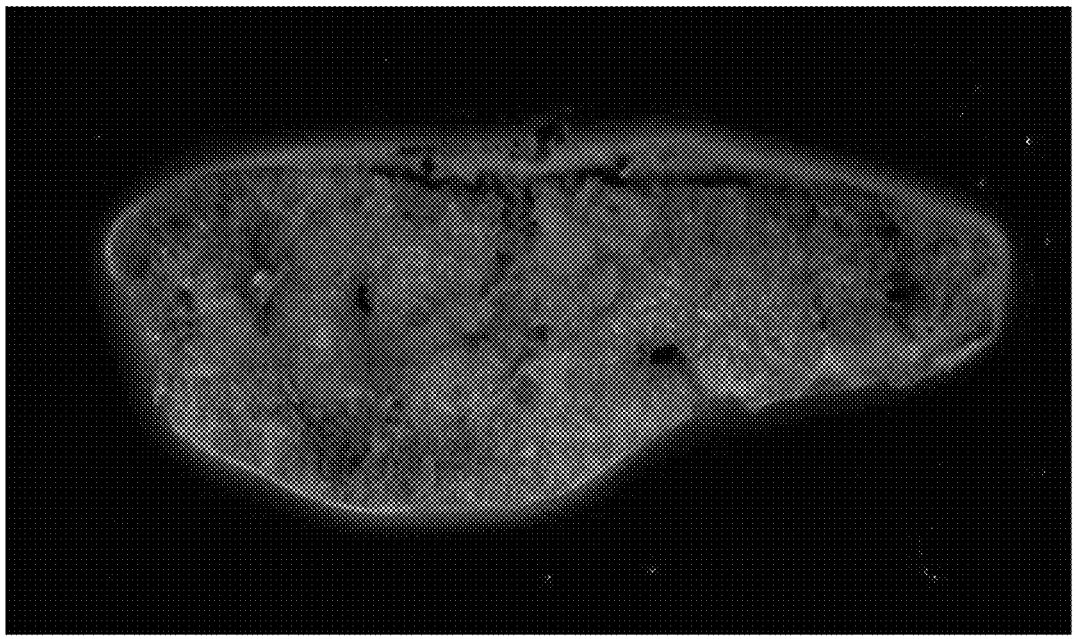
FIG. 8M shows an image obtained from simultaneous detection of three fluorescent dyes, one detectable at 488 nm, one detectable at 520 nm, and one detectable at 658 nm, from a chicken liver tissue sample consistent with one embodiment of the present disclosure.
Figure 8N:
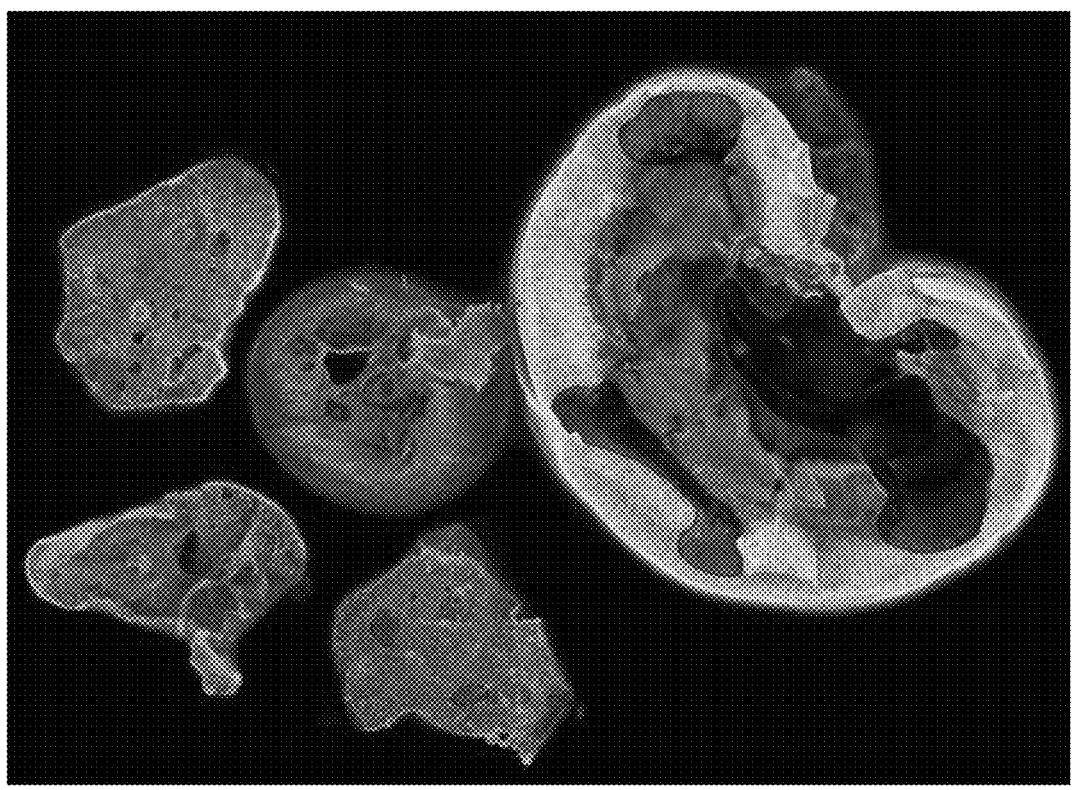
FIG. 8N shows an image obtained from simultaneous detection of two fluorescent dyes, one detectable at 658 nm and the other detectable at 785 nm, from a mixed tissue sample consistent with one embodiment of the present disclosure.

In some embodiments, the present disclosure provides a composite image comprising a first pattern having a first color, a second pattern having a second color, and a third pattern having a third color, wherein the first pattern corresponds to a pattern of first labeled biomolecules present in a 2D or 3D biological sample, the second pattern corresponds to a pattern of second labeled biomolecules present in the 2D or 3D biological sample, and wherein the third pattern corresponds to a pattern of third labeled biomolecules present in the 2D or 3D biological sample, wherein the first labeled biomolecules, the second labeled biomolecules, and the third labeled biomolecules are each different from each other. In some embodiments, the first labeled biomolecules are excitable at a first wavelength of light, the second labeled biomolecules are excitable at a second, different wavelength of light, and the third labeled biomolecules are excitable at a third, different wavelength of light. The images shown in FIGS. 8G, 8J and 8M are each consistent with such embodiments.

In some embodiments, the present disclosure provides a composite image comprising a first pattern having a first color, a second pattern having a second color, a third pattern having a third color, and a fourth pattern having a fourth color, wherein the first pattern corresponds to a pattern of first labeled biomolecules present in a 2D or 3D biological sample, the second pattern corresponds to a pattern of second labeled biomolecules present in the 2D or 3D biological sample, the third pattern corresponds to a pattern of third labeled biomolecules present in the 2D or 3D biological sample, and the fourth pattern corresponds to a pattern of fourth labeled biomolecules present in the 2D or 3D biological sample, wherein the first labeled biomolecules, the second labeled biomolecules, the third labeled biomolecules, and fourth labeled biomolecules are each different from each other. In some embodiments, the first labeled biomolecules are excitable at a first wavelength of light, the second labeled biomolecules are excitable at a second, different wavelength of light, the third labeled biomolecules are excitable at a third, different wavelength of light, and the fourth labeled biomolecules are excitable at a fourth, different wavelength of light. The image shown in FIG. 8H is consistent with such an embodiment.

In some embodiments, the present disclosure provides a detection instrument comprising a first excitation light source for illuminating a substrate; a second excitation light source for illuminating the substrate; a first detector for detecting light reflected or emitted by the substrate from the first excitation light source; and a second detector for detecting light reflected or emitted by the substrate from the second excitation light source. In some embodiments, the detection instrument further comprises an objective through which light from the first excitation light source and the second excitation light source pass before illuminating the substrate. In some embodiments, the detection instrument further comprises a first pair of dichroic beam splitters through which light from the first excitation light source passes before illuminating the substrate. In some embodiments, the detection instrument further comprises a second pair of dichroic beam splitters through which light from the second excitation light source passes before illuminating the substrate. In some embodiments, the detection instrument further comprises a first focus lens through which light reflected from the substrate passes before reaching the first detector. In some embodiments, the detection instrument further comprises a second focus lens through which light reflected from the substrate passes before reaching the second detector. In some embodiments, the detection instrument further comprises a first emission filter through which light reflected from the substrate passes before reaching the first detector. In some embodiments, the detection instrument further comprises a second emission filter through which light reflected from the substrate passes before reaching the second detector. In some embodiments, the detection instrument further comprises a first cleanup filter through which light from the first excitation light source passes before illuminating the substrate. In some embodiments, the detection instrument further comprises a second cleanup filter through which light from the second excitation light source passes before illuminating the substrate.

In some embodiments, the present disclosure provides a method of simultaneously detecting multiple fluorescent dyes in a biological substrate, the method comprising: contacting a substrate with more than one fluorescent dye; simultaneously illuminating the substrate with laser light comprising at least two wavelengths; and detecting an intensity of at least two wavelengths of light reflected from the substrate. In some embodiments, the method further comprises passing the laser light through at least two dichroic beam splitters before illuminating the substrate. In some embodiments, the method further comprises passing the laser light through an objective before illuminating the substrate. In some embodiments, the light reflected from the substrate passes through at least two emission filters before reaching at least two detectors. In some embodiments, the method further comprises passing the laser light through at least two cleanup filters before illuminating the substrate. In some embodiments, the light reflected from the substrate passes through at least two focus lenses before reaching at least two detectors. In some embodiments, the step of contacting the substrate comprises contacting the substrate with at least two dyes selected from the group consisting of: cyanine 3 (Cy3), cyanine 5 (Cy5), a near infrared (NIR) dye, Coomassie blue dye, ethidium bromide, and phosphorimaging dye. In some embodiments, the substrate is an electrophoresis gel. In some embodiments, the method comprises simultaneously illuminating the substrate with laser light comprising two wavelengths; and detecting an intensity of two wavelengths of light reflected from the substrate. In some embodiments, the method comprises simultaneously illuminating the substrate with laser light comprising three wavelengths; and detecting an intensity of three wavelengths of light reflected from the substrate. In some embodiments, the method comprises simultaneously illuminating the substrate with laser light comprising four wavelengths; and detecting an intensity of four wavelengths of light reflected from the substrate. In some embodiments, the step of detecting an intensity of at least two wavelengths of light reflected from the substrate comprises detecting an intensity of at least two wavelengths of light reflected from a plurality of points on a surface of the substrate. In some embodiments, the method further comprises displaying a first visual representation of the detected intensities of the at least two wavelengths of light as a first two-dimensional image. In some embodiments, the method further comprises illuminating the substrate with light from an LED light source; and detecting an intensity of at least one wavelength of light reflected or emitted off of the substrate. In some embodiments, the step of detecting an intensity of at least one wavelength of light reflected from the substrate comprises detecting an intensity of at least one wavelength of light reflected from a plurality of points on a surface of the substrate. In some embodiments, the method further comprises displaying a second visual representation of the detected intensities of the at least one wavelength of light as a second two-dimensional image. In some embodiments, the method further comprises combining the first visual representation and the second visual representation to form a composite two-dimensional image. In some embodiments, the method further comprises placing the substrate on a scanning bed in optical communication with the laser light; illuminating the substrate with light from an LED light source; and detecting boundaries of the substrate using a CCD camera. In some embodiments, the step of detecting boundaries of the substrate occurs before the step of simultaneously illuminating the substrate with laser light comprising at least two wavelengths, wherein the step of simultaneously illuminating the substrate with laser light comprising at least two wavelengths comprises illuminating only an area within the detected boundaries of the substrate with the laser light.

In some embodiments, the present disclosure provides a detection instrument capable of distinguishing between at least two types of molecules in a single substrate, the detection instrument comprising: a first optical path comprising a laser light source and a first detector for scanning the substrate with light having a first wavelength; and a second optical path comprising an LED light source and a second detector for capturing an image of the substrate at visible wavelengths. In some embodiments, the first optical path further comprises a dual-band emission filter for distinguishing between fluorescent emitted light and phosphorescent emitted light. In some embodiments, the detection instrument further comprises a third optical path comprising a second laser light source and a second detector for scanning the substrate with light having a second, different wavelength. In some embodiments, the detection instrument further comprises a fourth optical path comprising a third laser light source and a third detector for scanning the substrate with light having a third, different wavelength. In some embodiments, the detection instrument further comprises a fifth optical path comprising a fourth laser light source and a fourth detector for scanning the substrate with light having a fourth, different wavelength. In some embodiments, the first wavelength is selected from the group consisting of: 488 nm, 520 nm, 658 nm, and 784 nm. In some embodiments, the first wavelength and the second wavelength are different and independently selected from the group consisting of: 488 nm, 520 nm, 658 nm, and 784 nm. In some embodiments, the first wavelength, the second wavelength, and the third wavelength are different and independently selected from the group consisting of: 488 nm, 520 nm, 658 nm, and 784 nm. In some embodiments, the first wavelength, the second wavelength, the third wavelength, and the fourth wavelength are different and independently selected from the group consisting of: 488 nm, 520 nm, 658 nm, and 784 nm. In some embodiments, the first wavelength and the second wavelength are different and independently selected from the group consisting of: 658 nm and 784 nm. In some embodiments, the first wavelength, the second wavelength, and the third wavelength are different and independently selected from the group consisting of: 488 nm, 520 nm, and 658 nm. In some embodiments, the detection instrument further comprises a photomultiplier tube if any one of the optical paths comprises a laser light source that emits light at 488 nm or 520 nm. In some embodiments, the detection instrument further comprises an avalanche photodiode if any of the optical paths comprises a laser light source that emits light at 658 nm or 784 nm. In some embodiments, the first optical path and the third optical path are housed within a first scan head, and wherein the fourth optical path and the fifth optical path are housed within a second scan head that is optically distinct from the first scan head. In some embodiments, the second detector is a CCD camera.

In some embodiments, the present disclosure provides a composite image derived from a substrate, the composite image comprising: a first pattern having a first color and corresponding to a first pattern of a first type of molecule in the substrate; a second pattern having a second color and corresponding to a second pattern of a second type of molecule in the substrate; a third pattern having a third color and corresponding to a third pattern of a third type of molecule in the substrate, wherein the first color, the second color, and the third color are each different, wherein the first type of molecule is selected from the group consisting of: a molecule including a fluorescent label, a chemiluminescent molecule, a colorimetric molecule, and a phosphorescent molecule, wherein, the second type of molecule is different than the first type of molecule and is selected from the group consisting of: a molecule including a fluorescent label, a chemiluminescent molecule, a colorimetric molecule, and a phosphorescent molecule, with a first proviso that, if the first type of molecule is a chemiluminescent molecule, the second type of molecule is not a chemiluminescent molecule and the third type of molecule is not a chemiluminescent molecule, with a second proviso that, if the first type of molecule is a colorimetric molecule, the second type of molecule is not a colorimetric molecule and the third type of molecule is not a colorimetric molecule, and with a third proviso that, if the first type of molecule is a phosphorescent molecule, the second type of molecule is not a phosphorescent molecule and the third type of molecule is not a phosphorescent molecule. In some embodiments, the first pattern, the second pattern, and the third pattern are each derived from the substrate without moving the substrate. In some embodiments, at least two of the first type of molecule, the second type of molecule, and the third type of molecule includes a fluorescent label. In some embodiments, the first type of molecule includes a first fluorescent label, the second type of molecule includes a second fluorescent label, and the third type of molecule includes a third fluorescent label. In some embodiments, the composite image further comprises a fourth pattern having a fourth color and corresponding to a fourth pattern of a fourth type of molecule in the substrate, wherein the fourth type of molecule is selected from the group consisting of: a molecule including a fluorescent label, a chemiluminescent molecule, a colorimetric molecule, and a phosphorescent molecule, with a fourth proviso that, if any one of the first, second, or third types of molecules is a chemiluminescent molecule, then the fourth type of molecule is not a chemiluminescent molecule, with a fifth proviso that, if any one of the first, second, or third types of molecules is a colorimetric molecule, then the fourth type of molecule is not a colorimetric molecule, and with a sixth proviso that, if any one of the first, second, or third types of molecules is a phosphorescent molecule, then the fourth type of molecule is not a phosphorescent molecule. In some embodiments, the first type of molecule includes a first fluorescent label, the second type of molecule includes a second fluorescent label, the third type of molecule includes a third fluorescent label, and the fourth type of molecule includes a fourth fluorescent label. In some embodiments, at least one of the first pattern, the second pattern, and the third pattern is captured by an optical path comprising a laser light source and a photomultiplier tube or an avalanche photodiode. In some embodiments, the optical path further comprises a dual-band emission filter. In some embodiments, at least one of the first pattern, the second pattern, and the third pattern is captured by an optical path comprising an LED light source and a CCD camera. In some embodiments, at least one of the first pattern, the second pattern, and the third pattern has a resolution of 10 µm or less. In some embodiments, the substrate is an electrophoresis gel. In some embodiments, the substrate is a PVDF membrane. In some embodiments, the substrate is a multi-welled plate. In some embodiments, the substrate is a plant, an animal, or a portion of a plant or animal.

EXAMPLES

Aspects of embodiments may be further understood in light of the following examples, which should not be construed as limiting in any way.

Example 1. Using Dual Scan Head to Scan 4 Fluorescent Dyes Simultaneously

Cell Lysate prepared from HT-29 cell culture grown under standard conditions and treated with 500 ng/mL insulin are lysed in sodium dodecyl sulfate (SDS) containing Laemmle buffer and polyacrylamide gel electrophoresis (SDS-PAGE) is run on a 10% polyacrylamide gel for 1 hour at 1000V. Afterwards, separated proteins are transferred from gel onto PVDF membrane by electroblotting. The membrane is washed and blocked using standard procedures, and incubated with antibodies for 4 different cellular proteins, each labeled with a different fluorescent dye (Alexa Fluor® 488, Alexa Fluor® 532 Alexa Fluor® 633 and Alexa Fluor® 790, Thermo Fisher Scientific Inc., Pittsburgh, Pa.) for 2 hours at room temperature. The membrane is then rinsed with buffer and ready to load into detection instrument 200.

Optical components in scan head 1 of dual scan head 208 are outlined in FIG. 2. In this example, Alexa Fluor@ 532 will be excited using 525 nm diode laser as light source 118 and detected with a photomultiplier tube (PMT) as detector 122. Having an emission filter that is a single-bandpass 570/40 will allow light of wavelengths between 550 nm and 590 nm to reach the detector. And lastly beam splitter 114 is selected to pass wavelengths above 540 nm, and reflect light below 540 nm. Similarly, Alexa Fluor@ 790 will be excited using the components in FIG. 3 listed for NIR excitable dyes. By selecting a bandpass filter 112 that reflects light below 640 nm and passes light above 640 nm, these two dyes can be excited and detected simultaneously with the one scan head.

Scan head 2 is built using the components in FIG. 4 to excite and measure the Alexa Fluor@ 488 and Alexa Fluor@ 633.

The CCD detector 206 takes an image of the entire scan bed and embedded software processes the image to find the location of the blot on the scan bed. The optical scan heads then move to the location of the blot and begin to move along the length of the blot to measure fluorescence across the entire blot. The resulting scanned image is presented to the operator for analysis.

Example 2. RNA Binding Assay Using FIG. 2 Optical Setup

RNA samples separated on agarose gel by standard methods are transferred to nitrocellulose membrane and blocked according to standard methods before being probed with DNA labeled with $\alpha^{32}P$ labeled nucleotide. The membrane is then washed, wrapped in plastic wrap and placed on a phosphorimaging screen for 120 minutes to allow phosphor on plate to absorb energy from radiolabel. The phosphorimaging screen is then loaded onto scan bed of the instrument described in Example 1.

Optical scan head 2 has components outlined in FIG. 4. This setup was used as in the previous example to read red and blue dyes, but also can be used to scan a phosphorimaging screen. Here the phosphor on the screen will be excited using the 625 nm diode laser in light source position 120. The phosphor emits light at 400 nm after stimulation, which is captured through the objective, reflected by beam splitter 112, passes through beam splitter 114, and the dual band pass emission filter 108 through the focus lens 104 onto PMT detector 122.

The CCD detector 206 takes an image of the entire scan bed which is used to find the location of the blot on the scan bed. The optical scan heads then move to the location of the blot and begin to scan along both axes of the blot to measure fluorescence across the entire blot. The resulting scanned image is presented to the operator for analysis.

Example 3. Protein Gel Imaging with Optical Densitometry of Coomassie Blue Stained Gel Protein sample is separated on SDS-PAGE gel according to standard protocol and proteins are fixed in gel using a mixture of 25% isopropyl alcohol, 10% acetic acid for 60 minutes. The gel is then stained in a 60 mg/L solution of Coomassie Blue R-250 in 10% Acetic acid, and destained in 10% acetic acid to remove non-specifically bound Coomassie Blue.

The gel is then placed on the scanner bed in the same instrument used for examples 1, 2, and 3. Blue LED is used to illuminate gel, and CCD below gel measures light transmitted though gel. The resultant image can then be used to determine protein density at different location on gel.

Example 4. Chemiluminescent Gel Imaging

Cell lysate prepared from HT-29 cell culture grown under standard conditions and treated with 500 ng/mL insulin are lysed in sodium dodecyl sulfate (SDS) containing Laemmle buffer and polyacrylamide gel electrophoresis (SDS-PAGE) is run on a 10% polyacrylamide gel for 1 hour at 1000V. Afterwards, separated proteins are transferred from gel onto PVDF membrane by electroblotting. The membrane is washed and blocked using standard procedures, and incubated with anti-ERK primary antibody (Millipore 06-182) for 2 hours at room temperature. The membrane is washed and then incubated with Horseradish peroxidase (H RP) labeled anti-rabbit secondary antibody (ThermoFisher 81-6120) at 1:10,000 dilution for 30 minutes at room temperature. The membrane is then rinsed with buffer and ready to load into detection instrument 200.

The membrane is placed on scan bed 204, and covered with luminol and peroxide mixture (Cat #34075, Thermo Fisher Scientific Inc., Pittsburgh, Pa.) to initiate chemiluminescence. CCD 206 is used to capture an image of chemiluminescence. The resultant image can then be used to determine protein density at different location on gel.

Example 5. Using Dual Scan Head to Scan 4 Fluorescent Dyes Simultaneously

Cell lysate prepared from HT-29 cell culture grown under standard conditions and treated with 500 ng/mL insulin are lysed in sodium dodecyl sulfate (SDS) containing Laemmle buffer and polyacrylamide gel electrophoresis (SDS-PAGE) is run on a 10% polyacrylamide gel for 1 hour at 1000V. Afterwards, separated proteins are transferred from gel onto PVDF membrane by electroblotting. The membrane is washed and blocked using standard procedures, and incubated with antibodies for 4 different cellular proteins, each labeled with a different fluorescent dye (Alexa Fluor® 488, Alexa Fluor® 532 Alexa Fluor® 633 and Alexa Fluor® 790, Thermo Fisher Scientific Inc., Pittsburgh, Pa.) for 2 hours at room temperature. The membrane is then rinsed with buffer and ready to load into detection instrument 200.

Optical components in scan head 1 of dual scan head 208 are outlined in FIG. 2. In this example, Alexa Fluor@ 532 will be excited using 525 nm diode laser as light source 518 and detected with a photomultiplier tube (PMT) as detector 522. Having an emission filter that is a single-bandpass 570/40 will allow light of wavelengths between 550 nm and 590 nm to reach the detector. And lastly beam splitter 514 is selected to pass wavelengths above 540 nm, and reflect light below 540 nm. Similarly, Alexa Fluor@ 790 will be excited using the components in FIG. 3 listed for NIR excitable dyes. By selecting a bandpass filter 512 that reflects light below 640 nm and passes light above 640 nm, these two dyes can be excited and detected simultaneously with the one scan head.

Scan head 2 is built using the components in FIG. 4 to excite and measure the Alexa Fluor@ 488 and Alexa Fluor@ 633.

The CCD detector 206 takes an image of the entire scan bed and embedded software processes the image to find the location of the blot on the scan bed. The optical scan heads then move to the location of the blot and begin to move along the length of the blot to measure fluorescence across the entire blot. The resulting scanned image is presented to the operator for analysis.

Example 6. RNA Binding Assay Using FIG. 2 Optical Setup

RNA samples separated on agarose gel by standard methods are transferred to nitrocellulose membrane and blocked according to standard methods before being probed with DNA labeled with $\alpha^{32}P$ labeled nucleotide. The membrane is then washed, wrapped in plastic wrap and placed on a phosphorimaging screen for 120 minutes to allow phosphor on plate to absorb energy from radiolabel. The phosphorimaging screen is then loaded onto scan bed of the instrument described in Example 5.

Optical scan head 2 has components outlined in FIG. 4. This setup was used as in the previous example to read red and blue dyes, but also can be used to scan a phosphorimaging screen. Here the phosphor on the screen will be excited using the 625 nm diode laser in light source position 520. The phosphor emits light at 400 nm after stimulation, which is captured through the objective, reflected by beam splitter 512, passes through beam splitter 514, and the dual band pass emission filter 508 through the focus lens 504 onto PMT detector 522.

The CCD detector 206 takes an image of the entire scan bed which is used to find the location of the blot on the scan bed. The optical scan heads then move to the location of the blot and begin to scan along both axes of the blot to measure fluorescence across the entire blot. The resulting scanned image is presented to the operator for analysis.

Example 7. Simultaneous Visualization of Cy3 and Cy5 Labeled Lysate Components in a 2D Gel Untreated HeLa lysate was labeled with Cyanine Dye 3 ("Cy3") according to the dye manufacturer's instructions. The treated HeLa lysate was then labeled with Cyanine Dye 5 ("Cy5") according to the dye manufacturer's instructions. The double-labeled HeLa lysate was then loaded into a gel and separated using isoelectric focusing ("IEF") in one dimension and SDS-PAGE in a second, orthogonal dimension. The processed gel was imaged using a biomolecule scanner consistent with the present disclosure comprising a first laser emitting light at 520 nm and a second laser emitting light at 658 nm. The scanned gel is reproduced in FIG. 8A. The shorter wavelength light causes the Cy3-labeled HeLa lysate components to fluoresce a first, greenish color, while the longer wavelength light cases the Cy5-labeled HeLa lysate components to fluoresce a second, orange color.

Example 8. Simultaneous Visualization of Chemiluminescent and Fluorescent-Labeled Proteins A protein blot was prepared by performing gel electrophoresis using SDS-PAGE and standard Laemmli running buffer, followed by transfer to a PVDF membrane using transfer buffer (Azure Transfer Buffer #AC2127, Azure Biosystems Inc., Dublin, Calif.). The membrane was blocked for 30 minutes at room temperature using blot blocking buffer (Azure Chemi Blot Blocking Buffer #AC2148, Azure Biosystems Inc., Dublin, Calif.). The blot was then incubated for one hour at room temperature with chicken anti-Transferrin antibody in blot blocking buffer (Azure Chemi Blot Blocking Buffer #AC2148, Azure Biosystems Inc., Dublin, Calif.) with gentle agitation. The blot was then washed twice quickly, and then three more times for five minutes each, with at least 0.5 mL/cm$^2$ membrane blot washing buffer (Azure Blot Washing Buffer #AC2113, Azure Biosystems Inc., Dublin, Calif.). The blot was then incubated with anti-chicken secondary antibody in blot blocking buffer (Azure Chemi Blot Blocking Buffer #AC2148, Azure Biosystems Inc., Dublin, Calif.) for one hour at room temperature with gentle agitation, followed by washing twice quickly and three times for 5 minutes each as described above. A chemiluminescent HRP substrate (Radiance Chemiluminescent HRP Substrate #AC2101, Azure Biosystems Inc., Dublin, Calif.) was prepared according to the manufacturer's instructions and placed on the blot at 0.1 mL/cm$^2$ for two minutes. Excess chemiluminescent HRP substrate was drained and the blot was then imaged on a biomolecular scanner consistent with the present disclosure comprising 16×13 cm chemiluminescent imaging area having 16-bit, 2688-2200 resolution. The image is reproduced herein as FIG. 8B.

Example 9. Simultaneous Detection of Two Near-Infrared Fluorescent Labels

A protein blot was prepared by performing gel electrophoresis using SDS-PAGE and standard Laemmli running buffer, followed by transfer to a PVDF membrane using transfer buffer (Azure Transfer Buffer #AC2127, Azure Biosystems Inc., Dublin, Calif.). The membrane was blocked for 30 minutes at room temperature using blot blocking buffer (Azure Fluorescent Blot Blocking Buffer #AC2190, Azure Biosystems Inc., Dublin, Calif.). The blot was then incubated with mouse anti-STAT1 antibody and rabbit anti-phosphor-STAT1 antibody in a fluorescent blot blocking buffer (Azure Fluorescent Blot Blocking Buffer #AC2190, Azure Biosystems Inc., Dublin, Calif.) for one hour at room temperature with gentle agitation. The blot was then washed twice quickly, and then three more times for five minutes each, with at least 0.5 mL/cm$^2$ membrane fluorescent blot washing buffer (Azure Fluorescent Blot Washing Buffer #AC2145, Azure Biosystems Inc., Dublin, Calif.). The blot was the incubated with anti-mouse secondary antibody (AzureSpectra anti-mouse 700 secondary antibody #AC2129, Azure Biosystems Inc., Dublin, Calif.) and anti-rabbit secondary antibody (AzureSpectra anti-rabbit 800 secondary antibody #AC2134, Azure Biosystems Inc., Dublin, Calif.) in fluorescent blocking buffer (Azure Fluorescent Blot Blocking Buffer #AC2190, Azure Biosystems Inc., Dublin, Calif.) for one hour at room temperature with gentle agitation. The blot was then washed twice quickly and three times for five minutes each as described above, followed by rinsing for five minutes in PBS with at least 0.5 mL/cm$^2$ membrane. After drying, the membrane was imaged using a biomolecule scanner consistent with the present disclosure comprising a first laser emitting light at 658 nm and a second laser emitting light at 784 nm. The scanned image is reproduced herein as FIG. 8C, with the components labeled with anti-mouse secondary antibody appearing as red-orange bands, and the components labeled with anti-rabbit secondary antibody appearing as green bands.

Example 10. Simultaneous Visualization of Visible and Chemilumiescent Gel Bands Protein markers and a protein-containing test sample were separated on a gel using SDS-PAGE in Laemmli running buffer according to standard protocols well known in the art. The gel was then removed from the electrophoresis cassette and incubated in a tray with 25 mL of a rapid Coomassie stain (Generon Quick Coomassie Stain, Cat# GEN-QC-STAIN-1L, Generon Ltd, Slough UK) for one hour at room temperature. The gel was then relocated to ultra pure water for destaining. The destained gel was imaged on a biomolecule scanner consistent with the present disclosure comprising a LED lamp and CCD camera configured to capture visible light, and a laser source emitting light at a wavelength of 658 nm. The image is reproduced herein as FIG. 8D.

Example 11. Visualization of Small Quantities of Nucleic Acid Material in an Agarose Gel A 1:1 dilution series of molecular weight ladders in water was prepared according to standard protocols well known in the art. Agarose gels (0.8%) were cast in 1×TAE with ethidium bromide ("EtBr") at a ratio of 1:10,000 according to standard protocols well known in the art. 10 μL of each dilution was loaded into a well of the agarose gel. Separation of the molecular weight ladder samples occurred at 70V for 120-150 minutes in 1×TAE. Once electrophoretic separation was complete, the gels were imaged using a biomolecule scanner consistent with the present disclosure comprising a laser emitting light at 520 nm. A representative scanned image is reproduced herein as FIG. 8E, with the left lane having a mass of 1250 pg (arrow) and the far right lane having a mass of 20 pg (arrow).

Example 12. Flimless Autoradiography of Phosphor-Radiolabeled Biomolecules

A commercially available carbon-14 standard including slices ranging from 0.004 μCi/g to 1,000 μCi/g (Cat # ARC0146F, American Radiolabeled Chemicals, Inc., St. Louis, Mo.) was exposed to a BAS-MS storage phosphor screen having a sensitivity of 0.9 DPM/mm$^2$/hr (Cat #IS1011, Azure Biosystems Inc., Dublin, Calif.) for three hours. The storage phosphor screen was then imaged using a biomolecule scanner consistent with the present disclosure comprising a laser emitting light at 658 nm and a photomultiplier tube detector. The limit of detection was determined to be only 0.036 μCi/g, and the detection was linear ($R^2$=0.99) over 5.4 orders of magnitude. The scanned image is reproduced herein as FIG. 8F.

Example 13. Detection of Proteins In-Situ by In-Cell Western Blotting

HeLa cells were serially diluted and seeded into a sterile 96-well tissue culture plate at a volume of 0.2 mL/well, and grown until approximately 80% confluent. All wells were then fixed and permeabilized using 100% methanol for 15 minutes at room temperature. Cells were then rinsed with PBS and blocked with 1% fish gelatin in PBS for one hour at room temperature. The blocked cells were then probed with mouse alpha-tubulin and rabbit beta-actin overnight at 4° C. Wells were then washed three times each with PBS prior to incubation with an anti-rabbit conjugated secondary antibody (AzureSpectra anti-rabbit 550, Cat #AC2158, Azure Biosystems Inc., Dublin, Calif.) and an anti-mouse conjugated secondary antibody (AzureSpectra anti-mouse 800 conjugated secondary antibody, Cat #AC2135, Azure Biosystems Inc., Dublin, Calif.) for 60 minutes at room temperature. Cells in all wells were then stained with a far-red cell membrane-permeable nuclear dye (RedDot™1, Cat #40060-1, Biotium, Inc., Fremont, Calif.) consistent with the manufacturer's instructions as a normalization control. Wells were then washed three times with PBS. The wells were scanned at multiple wavelengths using a biomolecule scanner consistent with the present disclosure comprising an LED emitting light at 520 nm, a first laser emitting light at 658 nm, and a second laser emitting light at 785 nm, a photomultiplier tube detector, and an avalanche photodiode detector. The captured images for each of the three excitation wavelengths were combined into a single composite image, which is reproduced herein as FIG. 8G.

Example 14. Simultaneous Detection of Four Different Fluorescent Probes

A protein blot was prepared from HeLa cell samples or HeLa cell samples spiked with transferrin by 4-15% trisglycine gel electrophoresis using SDS-PAGE and standard Laemmli running buffer, followed by transfer to low-fluorescence PVDF membrane (Cat #AC2105, Azure Biosystems Inc., Dublin, Calif.) using transfer buffer (Azure Transfer Buffer #AC2127, Azure Biosystems Inc., Dublin, Calif.). The membrane was blocked for 30 minutes at room temperature using blot blocking buffer (Azure Fluorescent Blot Blocking Buffer #AC2190, Azure Biosystems Inc., Dublin, Calif.). The blot was then incubated with anti-transferrin antibody (Cat #AC2185, Azure Biosystems Inc., Dublin Calif.) labeled with fluorescent dye excitable at ~490 nm that emits at ~515 nm (AzureSpectra 490, Cat #AC2185, Azure Biosystems Inc., Dublin, Calif.), goat anti-rat tubulin (Cat #AC2162, Azure Biosystems Inc., Dublin, Calif.), goat anti-rabbit actin (Cat #AC2128, Azure Biosystems Inc., Dublin, Calif.), and goat anti-chicken GAPHD (Cat #AC2137, Azure Biosystems Inc., Dublin, Calif.) in blot blocking buffer (Azure Fluorescent Blot Blocking Buffer #AC2190, Azure Biosystems Inc., Dublin, Calif.) for one hour at room temperature with gentle agitation. The blot was washed twice quickly and three times for five minutes each with at least 0.5 ml/cm$^2$ membrane fluorescent blot washing buffer (Azure Fluorescent Blot Washing Buffer, Cat #AC2190, Azure Biosystems Inc., Dublin, Calif.). The washed blot was then incubated with anti-rat, anti-rabbit and anti-chicken secondary antibodies (Cat Nos. AC2162, AC2128 and AC2137, respectively, Azure Biosystems Inc., Dublin, Calif.) in fluorescent blot blocking buffer (Azure Fluorescent Blot Blocking Buffer, Cat #AC2190, Azure Biosystems Inc., Dublin, Calif.) for one hour at room temperature with gentle agitation. The labeled blot was then washed twice quickly and three times for five minutes each as described above, and then rinsed for five minutes with at least 0.5 mL/cm$^2$ PBS. The membrane was then dried and imaged using a biomolecule scanner consistent with the present disclosure comprising a first laser emitting light at 488 nm and a second laser emitting light at 520 nm, a third laser emitting light at 658 nm, and a fourth laser emitting light at 784 nm; a photomultiplier tube detector and an avalanche photodiode detector. The scanned image is reproduced herein as FIG. 8H, with the GADPH components appearing as green bands, the actin components appearing as red bands, the tubulin bands appearing as blue bands, and the transferrin components appearing as white bands (from bottom to top).

Example 15. Simultaneous High-Resolution Imaging of Multiple Fluorescent Tags A scanner calibration slide including a first array of spots in two-fold dilution series of Cy3 fluorescent dye and a second array of spots in two-fold dilution series of Cy5 fluorescent dye, with a spot center-to-center distance of 350 µm (Cat #DS01, Full Moon BioSystems, Inc., Sunnyvale, Calif.) was scanned at 10 µm resolution by excitation at 520 nm and 658 nm simultaneously using a biomolecule scanner consistent with the present disclosure comprising a first laser emitting light at 520 nm and a second laser emitting light at 658 nm. The captured images for each of the two excitation wavelengths were combined into a single composite image, which is reproduced herein as FIG. 8I.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

It is to be understood that both the foregoing descriptions are exemplary and explanatory only, and are not restrictive of the methods and devices described herein. In this application, the use of the singular includes the plural unless specifically stated otherwise. Also, the use of "or" means "and/or" unless stated otherwise. Similarly, "comprise," "comprises," "comprising," "include," "includes" and "including" are not intended to be limiting.

All patents, patent applications, publications, and references cited herein are expressly incorporated by reference to the same extent as if each individual publication or patent application was specifically and individually indicated to be incorporated by reference.

What is claimed is:

1. A detection instrument capable of distinguishing between at least two types of molecules in a single substrate, the detection instrument comprising:
    a first optical path consisting essentially of: a laser light source, a pair of beam splitters, an objective, an emission filter, a focusing lens, and a first detector for scanning the substrate with light having a first wavelength; and
    a second optical path comprising an LED light source and a second detector for capturing an image of the substrate at visible wavelengths.

2. The detection instrument of claim 1, wherein the first optical path further comprises a dual-band emission filter for distinguishing between fluorescent emitted light and phosphorescent emitted light.

3. The detection instrument of claim 1 further comprising a third optical path comprising a second laser light source and a second detector for scanning the substrate with light having a second, different wavelength.

4. The detection instrument of claim 1 further comprising a fourth optical path comprising a third laser light source and a third detector for scanning the substrate with light having a third, different wavelength.

5. The detection instrument of claim 4 further comprising a fifth optical path comprising a fourth laser light source and a fourth detector for scanning the substrate with light having a fourth, different wavelength.

6. The detection instrument of claim 1, wherein the first wavelength is selected from the group consisting of: 488 nm, 520 nm, 658 nm, and 784 nm.

7. The detection instrument of claim 3, wherein the first wavelength and the second wavelength are different and independently selected from the group consisting of: 488 nm, 520 nm, 658 nm, and 784 nm.

8. The detection instrument of claim 4, wherein the first wavelength, the second wavelength, and the third wavelength are different and independently selected from the group consisting of: 488 nm, 520 nm, 658 nm, and 784 nm.

9. The detection instrument of claim 5, wherein the first wavelength, the second wavelength, the third wavelength, and the fourth wavelength are different and independently selected from the group consisting of: 488 nm, 520 nm, 658 nm, and 784 nm.

10. The detection instrument of claim 3, wherein the first wavelength and the second wavelength are different and independently selected from the group consisting of: 658 nm and 784 nm.

11. The detection instrument of claim 4, wherein the first wavelength, the second wavelength, and the third wavelength are different and independently selected from the group consisting of: 488 nm, 520 nm, and 658 nm.

12. The detection instrument of claim 1 further comprising a photomultiplier tube if any one of the optical paths comprises a laser light source that emits light at 488 nm or 520 nm.

13. The detection instrument of claim 1 further comprising an avalanche photodiode if any of the optical paths comprises a laser light source that emits light at 658 nm or 784 nm.

14. The detection instrument of claim 5, wherein the first optical path and the third optical path are housed within a first scan head, and wherein the fourth optical path and the fifth optical path are housed within a second scan head that is optically distinct from the first scan head.

15. The detection instrument of claim 1, wherein the second detector is a CCD camera.

* * * * *